United States Patent
Jamil et al.

(10) Patent No.: US 8,639,639 B2
(45) Date of Patent: Jan. 28, 2014

(54) PREDICTING POSSIBLE OUTCOMES IN MULTI-FACTORED DISEASES

(75) Inventors: Kaiser Jamil, Andhra Pradesh (IN); Haranatha P. Reddy, Andhra Pradesh (IN); Subrahmanya K. Nairy, Andhra Pradesh (IN)

(73) Assignee: Bhagwan Mahavir Medical Research Centre, Hyderabad (IN)

(*) Notice: Subject to any disclaimer, the term of this patent is extended or adjusted under 35 U.S.C. 154(b) by 953 days.

(21) Appl. No.: 12/624,374

(22) Filed: Nov. 23, 2009

(65) Prior Publication Data

US 2011/0055141 A1 Mar. 3, 2011

(30) Foreign Application Priority Data

Aug. 31, 2009 (IN) .......................... 2104/CHE/2009

(51) Int. Cl.
  *G06F 15/18* (2006.01)
  *G06N 99/00* (2010.01)
  *G06K 9/62* (2006.01)

(52) U.S. Cl.
  CPC ............ *G06N 99/005* (2013.01); *G06K 9/6234* (2013.01)
  USPC .......................................................... 706/12

(58) Field of Classification Search
  USPC ..................................... 706/45–58; D24/186
  See application file for complete search history.

(56) References Cited

U.S. PATENT DOCUMENTS

| | | | | |
|---|---|---|---|---|
| 6,278,464 | B1* | 8/2001 | Kohavi et al. | 345/440 |
| 7,458,936 | B2* | 12/2008 | Zhou et al. | 600/437 |
| 8,306,942 | B2* | 11/2012 | Chen et al. | 706/62 |
| 2004/0215430 | A1* | 10/2004 | Huddleston et al. | 703/2 |

OTHER PUBLICATIONS

Ahn, Hongshik et al.; "Classification by ensembles from random partitions of high-dimensional data"; 2007; Computational Statistics & Data Analysis 51; pp. 6166-6179.*

Mandelblatt, Jeanne et al.; "The Late-State Diagnosis of Colorectal Cancer: Demographic and Socioeconomic Factors"; 1996; American Journal of Public Health vol. 86, No. 12; pp. 1794-1797.*

Ravina, Bernard et al.; "Diagnostic Criteria for Psychosis in Parkinson's Disease: Report of an NINDS, NIMH Work Group"; 2007; Wiley; Movement Disorders vol. 22, No. 8; pp. 1061-1068.*

Balion, Cynthia M. et al.; "Physiological, pathological, pharmacological, biochemical and hematological factors affecting BNP and NT-proBNP"; 2008; Elsevier; Clinical Biochemistry 41; pp. 231-239.*

Lemon, Stephenie C. et al.; "Classification and Regression Tree Analysis in Public Health: Methodological Review and Comparison With Logistic Regression"; 2003; Annals of Behavioral Medicine 26.3; pp. 172-181.*

Ture, Mevlut et al.; "Using Kaplan-Meier analysis together with decision tree methods (C&RT, CHAID, QUEST, C4.5 and ID3) in determining recurrence-free survival of breast cancer patients"; Mar. 2009; Elsevier; Expert Systems with Applications 36; pp. 2017-2026.*

(Continued)

*Primary Examiner* — Jeffrey A Gaffin
*Assistant Examiner* — Stanley K Hill
(74) *Attorney, Agent, or Firm* — Foley & Lardner LLP

(57) ABSTRACT

This disclosure relates, in general, to methods, systems, apparatus, computer programs and computing devices related to predicting possible outcomes in a multi-factored disease, disorder or condition.

22 Claims, 14 Drawing Sheets

(56) References Cited

OTHER PUBLICATIONS

Biggs, D. et al., "A method of choosing multiway partitions for classification and decision trees," Journal of Applied Statistics, 1991, vol. 18, No. 1, pp. 49-62.

Kass, G.V., "An Exploratory Technique for Investigating Large Quantities of Categorical Data," Applied Statistics, 1980, vol. 29, No. 2, pp. 119-127.

Morgan, J.N. et al., "Problems in the analysis of survey data, and a proposal," Journal of the American Statistical Association, 1963, vol. 58, pp. 415-434.

Naoe, T. et al., "Analysis of Genetic Polymorphism in Nq01, GST-M1, GST-T1, and CYP3A4 in 469 Japanese Patients with Therapy-related Leukemia/Myelodysplastic Syndrome and de novo Acute Myeloid Leukemia," Clinical Cancer Research, Oct. 2000, vol. 6, pp. 4091-4095.

Ribeiro, R.C. et al., "Prognostic factors in childhood acute lymphoblastic leukemia," Hematol. Pathol., 1993, vol. 7, No. 3, pp. 121-142.

Baccarani et al., Adolescent and Adult Acute Lymphoblastic Leukemia: Prognostic Features and Outcome of Therapy. A Study of 293 Patients., Blood, 1982, vol. 60, pp. 677-684, American Society of Hematology, Washington, D.C.

Chen et al., Higher Frequency of Glutathione S-Transferase Deletions in Black Children with Acute Lymphoblastic Leukemia, Blood, 1987, vol. 89, pp. 1701-1707, American Society of Hematology, Washington, D.C.

Crist et al., Clinical and Biologic Features Predict a Poor Prognosis in Acute Lymphoid Leukemias in Infants: a Pediatric Oncology Group Study, Blood, 1986, vol. 67, pp. 135-140, American Society of Hematology, Washington, D.C.

Deakin et al., Glutathione S-Transferase GSTT1 Genotypes and Susceptibility to Cancer: Studies of Interactions with GSTM1 in Lung, Oral, Gastric and Colorectal Cancers, Carcinigenesis, 1996, vol. 17, No. 4, pp. 881-884, Oxford University Press.

Small et al., STK-1, the Human Homolog of Flk-2/Flt-3, is Selectively Expressed in CD34+ Human Bone Marrow.Cells and is Involved in the Proliferation of Early Progenitor/Stem Cells, Proc. Natl. Acad. Sci. USA, Jan. 1994, vol. 91, pp. 459-463, Cell Biology.

Frosst et al., A Candidate Genetic Risk Factor for Vascular Disease: a Common Mutation in Methylenetetrahydrofolate Reductase, Nature Genetics, May 1995, vol. 10, pp. 111-113.

Reddy et al., Polymorphisms in the GST (M1 and T1) Gene and Their Possible Association with Susceptibility to Childhood Acute Lymphocytic Leukemia in Indian Population, African Journal of Biotechnology, Aug. 17, 2006, vol. 5, No. 16, pp. 1454-1456, Academic Journals.

Reddy et al., Polymorphisms in the MTHFR Gene and Their Possible Association with Susceptibility to Childhood Acute Lymphocytic Leukemia in an Indian Population, Leukemia & Lymphoma, Jul. 2006, vol. 47, No. 7, pp. 1333-1339, Informa UK Ltd.

Hoelzer et al., Prognostic Factors in a Multicenter Study for Treatment of Acute Lymphoblastic Leukemia in Adults, Blood, 1988, vol. 71, pp. 123-131, American Society of Hematology, Washington, D.C.

Sawyers et al., Leukemia and the Disruption of Normal Hematopoiesis, Cell, Jan. 25, 1991, vol. 64, pp. 337-350, Cell Press.

Kuilenburg et al., Lethal 5-Fluorouracil Toxicity Associated with a Novel Mutation in the Dihydropyrimidine Dehydrogenase Gene, Annals of Oncology, 2003, vol. 14, pp. 341-342, European Society for Medical Oncology.

Wheatley et al., A Simple, Robust, Validated and Highly Predictive Index for the Determination of Risk-Directed Therapy in Acute Myeloid Leukaemia Derived from the MRC AML 10 Trial, British Journal of Haematology, 1999, vol. 107, pp. 69-79, Blackwell Science Ltd.

Tiesmeier et al., Evolution of FLT3-ITD and D835 Activating Point Mutations in Relapsing Acute Myeloid Leukemia and Response to Salvage Therapy, Leukemia Research, 2004, vol. 28, pp. 1069-1074, Elsevier Ltd.

Kim et al., Classification Trees with Unbiased Multiway Splits, J. Amer. Statist. Assoc., 2001, vol. 96, pp. 598-604.

Loh et al., Tree-Structured Classification Via Generalized Discriminant Analysis, Journal of the American Statistical Association, Sep. 1988, vol. 83, No. 403, pp. 715-728, Theory and Methods.

Loh et al., Split Selection Methods for Classification Trees, Statistica Sinica, 1997, vol. 7, pp. 815-840.

Loh et al., Regression Trees with Unbiased Variable Selection and Interaction Detection, Statistica Sinica, 2002, vol. 12, pp. 361-386.

Robbins and Angell, "Basic Pathology," Second Edition, W.B. Saunders Co., Philadelphia, 1976, pp. 349-354.

Van Kuilenburg, A.B.P., et al., "Novel disease-causing mutations in the dihydropyrimidine dehydrogenase gene interpreted by analysis of the three-dimensional protein structure," Biochem J, vol. 364, Biochemical Society, pp. 157-163 (2002).

* cited by examiner

Generating a graphical illustration of at least one of (a) the classification tree of two or more diagnostic factors of the multi-factored disease, disorder or condition, and (b) the discriminant analysis of the two or more diagnostic factors 5100 Generating the graphical illustration for inclusion in a display element of a graphical user interface 5101 Performing an analysis of at least one of the classification tree and the discriminant analysis 5102 Generating the graphical illustration based on the analysis

FIG. 10

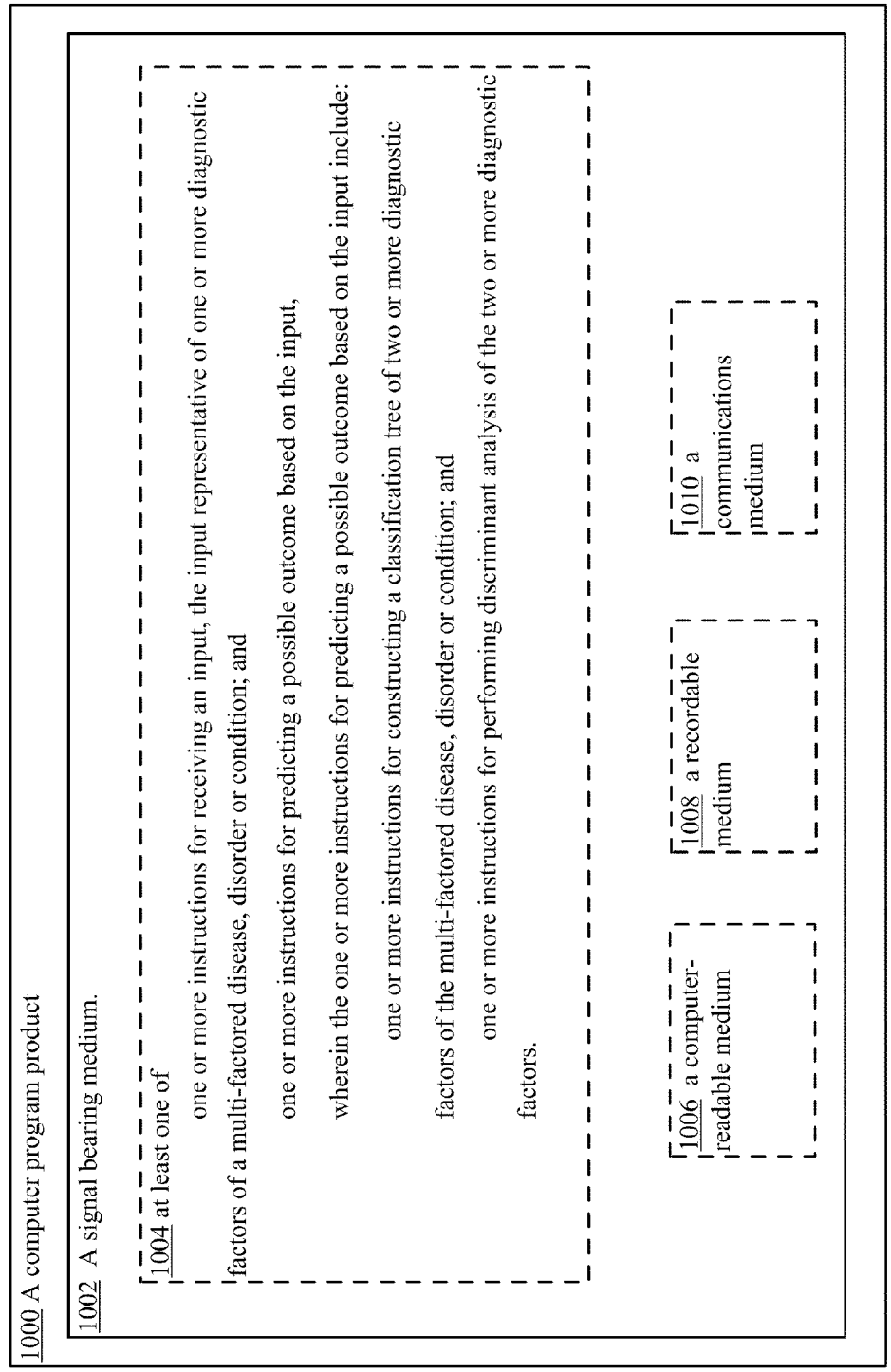

1000 A computer program product

1002 A signal bearing medium.

1004 at least one of
one or more instructions for receiving an input, the input representative of one or more diagnostic factors of a multi-factored disease, disorder or condition; and
one or more instructions for predicting a possible outcome based on the input,
wherein the one or more instructions for predicting a possible outcome based on the input include:
one or more instructions for constructing a classification tree of two or more diagnostic factors of the multi-factored disease, disorder or condition; and
one or more instructions for performing discriminant analysis of the two or more diagnostic factors.

1006 a computer-readable medium 1008 a recordable medium 1010 a communications medium

PREDICTING POSSIBLE OUTCOMES IN MULTI-FACTORED DISEASES

CROSS REFERENCE TO RELATED APPLICATIONS

The present application claims the benefit of Indian Patent Application No. 2104/CHE/2009, filed Aug. 31, 2009, which is hereby incorporated by reference in its entirety.

BRIEF DESCRIPTION OF THE FIGURES

FIG. 7 shows optional embodiments of the operational flow of FIG. 1 and/or FIG. 2.

FIG. 10 and FIG. 11 show partial views of illustrative embodiments of computer program products that includes a computer program for executing a computer process on a computing device.

DETAILED DESCRIPTION

Figure 1:
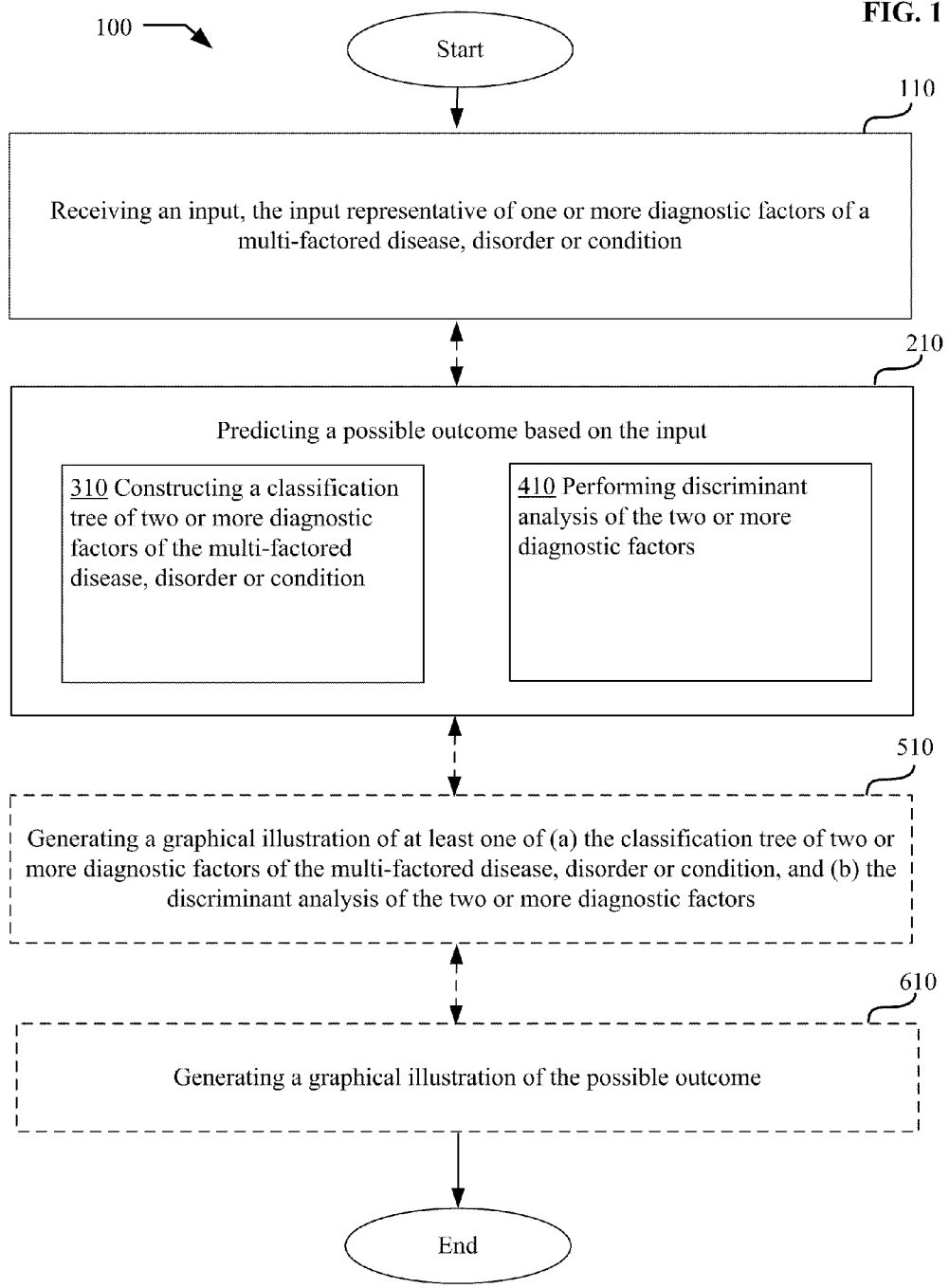
FIG. 1 and FIG. 2 show operational flows representing illustrative embodiments of operations related to predicting possible outcomes in multi-factored diseases, disorders or conditions.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

This disclosure relates, in general, to methods, systems, apparatus, computer programs and computing devices related to predicting possible outcomes in a multi-factored disease, disorder or condition. More particularly, the methods, systems, apparatus, computer programs and computing devices relate to the use of prognostic factors to predict possible outcomes. For example, the prediction may relate to the prognosis of the disease, disorder or condition. A more accurate prognosis is useful to improve survivability and employ better treatment protocols at the time of diagnosis. This may, for example, decrease the toxicity burden of drugs used in treatment and may, therefore, be of economic and clinical benefit to the patient or subject.

In order to better understand the detailed description and claims, the usage of some terms is provided below, unless context clearly dictates otherwise.

As used herein, the term "multi-factored disease(s), disorder(s) or condition(s)" means diseases, disorders or conditions that have, involve or result from more than one "element" or cause. All elements and/or causes of the diseases, disorders or conditions need not be definitely known. In some embodiments, a cause or causes may be unknown or not well-understood. In some embodiments, the diseases, disorders or conditions have, involve or result from 3 or more elements or causes. In some embodiments, the diseases, disorders or conditions have, involve or result from 4 or more elements or causes. In other embodiments, the diseases, disorders or conditions have, involve or result from 5, 6, 7, 8, 9, etc. or more elements or causes.

Examples of multi-factored diseases, disorders and conditions include, but are not limited to, cancers (such as leukemia and cancers of the bladder, brain, breast, colon, esophagus, kidney, liver, lung, mouth, ovary, pancreas, prostate, skin, stomach and uterus), autoimmune diseases (such as rheumatoid arthritis, systemic lupus erythematosus, and Grave's disease), cardiovascular diseases (such as angina pectoris, myocardial infarcation, heart disease, cardiomyopathies, and dsyrthythmias), infectious diseases (such as AIDS, Lyme disease, bacterial meningitis, bacteremia and sepsis, sexually transmitted diseases, and osteomyelitis), endocrinological disorders (such as diabetes, hypoglycemia, anterior pituitary disorders, thyroid disorders, and adrenal gland disorders), developmental abnormalities (such as congenital heart defects and neural tube defects), mental disorders (such as bipolar disorder, schizophrenia and other conditions well-documented in the DSM-IV-TR), neurological disorders (such as Alzheimer's disease, epilepsy, brain injuries, Parkinson's disease, and multiple sclerosis), inflammatory disorders (such as asthma, inflammatory bowel disease, and atopy), and obesity and eating disorders. This list is illustrative, and a person of ordinary skill in the art will recognize that many other diseases, disorders, and conditions involve or result from multiple elements or causes.

As used herein, "element(s)" refers generally to details, characteristics, parameters, features or qualities of the disease, disorder or condition. Examples of elements include, but are not limited to, complications, presentations, manifestations, signs, symptoms, physiologic parameters, tests, prophylaxis, medications, side effects therapies, and treatments. For example, common diagnostic tests associated with cancers include, but are not limited to, biopsy, CT scans, blood chemistries, and X-rays. Examples of treatments include, but are not limited to, surgery, chemotherapy, radiation therapy, immunotherapy, monoclonal antibody therapy, and photodynamic therapy. Other characteristics and features related to cancers may include, but are not limited to, malignancy, grade (e.g., 1, 2, 3, or 4), stage (e.g., 1, 2, 3, or 4), nodal status, tumor location and size, and metastasis. A person of ordinary skill in the art will recognize specific elements, such as symptoms, diagnostics tests, treatment options and other characteristics and features, that are relevant to a particular cancer. Moreover, the person of ordinary skill in the art will also recognize elements that are relevant to other diseases, disorders, and conditions.

As used herein, "diagnostic factor(s)" means elements related to the disease, disorder or condition that are relevant to predicting "possible outcomes." For example, they can include, but are not limited to, physical attributes, genetic characteristics, demographic factors, environmental factors, physiological data, and symptoms.

As used herein, "possible outcome(s)" means potential events related to a disease, disorder or condition. Examples include, but are not limited to, diagnosis, prognosis, possible risk, possible result, possible consequence, likelihood of success, result of a course of treatment, existence or non-existence of a characteristic or feature of the disease, achievement of a milestone, or cost.

For example, some embodiments relate to predicting prognosis of patients having multi-factored diseases, disorders, or conditions (e.g., cancers or autoimmune diseases). A person of ordinary skill in the art will recognize that appropriate descriptions of prognosis depend of the particular disease, disorder, or condition. In illustrative embodiments, a patient's prognosis may be classified according to survivability, intensity and/or duration of complications, risk, life expectancy, a scoring system, or a group of terms descriptive of prognosis. For example, in some embodiments, a prognosis can be classified as either (1) resistant to treatment, (2) relapse, or (3) disease-free survival. In some embodiments, a prognosis may be described in terms of the complications that may occur. For example, a prognosis may specify one or more complications and an predicted intensity or duration, such as acute, chronic, or a specific period of time. A person of ordinary skill in the art will recognize the complications that are associated with a given disease, disorder, or condition and the possible intensities and durations that may be experienced. In some embodiments, prognosis can be described using one or more terms that refer to the patient's chances for recovery, improvement, survival, etc., such as excellent, good, fair, poor, and very poor. In some embodiments, prognosis can be described using one or more terms that refer to the patient's risk of disease, deterioration, death, etc., such as low risk, intermediate risk, intermediate-high risk, and high risk.

In some embodiments, prognosis can be described using probabilities. For example, the probabilities may be expressed as percentages and refer to risk, survivability, life expectancy, etc. In illustrative embodiments, prognosis is expressed as the probability of survival for a certain period of time, such as 2-year survival of 75%, 2-year survival of 50%, 2-year survival of 25%, or 2-year survival of 5%.

In some embodiments, prognosis is described using a scoring system, such as standardized systems (e.g., the International Prognostic Index, including the Follicular Lymphoma International Prognostic Index and the Follicular Lymphoma International Prognostic Index, and the Manchester scoring system).

In some embodiments, the prediction of prognosis may be given as a range, such as a range of descriptive terms, probability, or score. For example, in illustrative embodiments, the prognosis may be excellent to good, poor to very poor, 50-60%, 5-year survival of 25-35%, 0-1, or 0-2.

In some embodiments, the disease, disorder, or condition may be unknown or uncertain. Thus, the disclosed embodiments may relate to providing an improved diagnosis based on the analysis of diagnostic factors. In some embodiments, the possible outcome may be the consequences of different treatment options, such as their effectiveness or the likelihood of side effects. Thus, the disclosed embodiments may assist a clinician in choosing the most desirable or effective course of treatment based on an analysis of diagnostic factors.

For example, recommended treatments for leukemia can vary according to prognosis, blood analysis, cancer stage, age, and physical condition, among other factors. As one illustrative example, a phased treatment of ALL in adults typically calls first for the administration of a drug plan containing prednisone, vincristine, and an anthracycline drug (L-asparaginase or cyclophosphamide may also be administered). A phased treatment in children typically calls first for the administration of prednisone, L-asparaginase, and vincristine. The initial phase is followed by therapy with antimetabolite drugs, such as methotrexate and 6-mercaptopurine, where the dosage and duration of therapy depend on age and the severity of ALL. Further preventative therapy and maintenance treatments may be provided based on the factors mentioned above in addition to revised prognosis. Thus, analysis of these and other diagnostic factors may assist a clinician in prescribing the most appropriate course of treatment for a patient having ALL.

As used herein, the term "physical attribute(s)" means any measurable, detectable, and/or identifiable physical characteristic. Examples include, but are not limited to, characteristics associated with disease state, body type, vision, strength, coordination, fertility, weight, skin, skeleto-muscular, longevity, and hair. In illustrative embodiments, physical attributes related to cancers include, but are not limited to, swelling, weight changes, hair loss, bruising, skin wounds, and skin coloration. For example, physical attributes associated with leukemia include, but are not limited to, vomiting, seizures, confusion, muscle control, hair thickness, diarrhea, and skin condition. The person of ordinary skill in the art will recognize other physical attributes that are relevant to particular cancers, as well as those that are relevant to other diseases, disorders, and conditions.

As used herein, the term "genetic characteristic(s)" refers to features associated with the inheritance of physical traits, including, but not limited to features associated with genes, alleles, chromosomes, DNA, or RNA. In some embodiments, they may relate to gene sequences, mutations, abnormalities, inversions, insertions, deletions, substitutions, duplications, single nucleotide polymorphisms, haplotypes, centromeres, telomeres, methylation patterns, introns, and exons. In illustrative embodiments, genetic characteristics related to cancers include, but are not limited to, RB1 (retinoblastoma 1), BRCA1 (breast cancer 1), BRCA2 (breast cancer 2), EGFR (epidermal growth factor receptor), MYC (myelocytomatosis), BCR (breakpoint cluster region), ABL (Abelson), BCR-ABL, ACE (angiotensin I converting enzyme), p53 (tumor protein 53), CDKN2A (Cyclin-dependent kinase inhibitor 2A), APC (adenomatosis polyposis coli), MLH1 (MutL homolog 1), MSH2 (MutL homolog 2), MSH6 (MutL homolog 6), WTI (Wilms' tumor), NF1 (neurofibromatosis 1), NF2 (neurofibromatosis 2), and VHL (Von Hippel-Lindau). The person of ordinary skill in the art will recognize other genetic characteristics that are relevant to particular cancers, as well as those that are relevant to other diseases, disorders, and conditions.

As used herein, the term "demographic factor(s)" are features associated with a population. Such factors include, but are not limited to race, ethnicity, age, sex, education level, income level, marital status, employment status, occupation, religion, location, family size, and exposure profile to environmental factors. In illustrative embodiments, demographic factors related to cancers include, but are not limited to, gender, age, race, ethnicity, diet, smoking, alcohol consumption, weight change, socioeconomic status, occupation, and residence. In some embodiments, demographic factors associated with leukemia in children include, but are not limited to, maternal history of fetal loss, parents' age, birth weight, and nutrition. A person of ordinary skill in the art will recognize other demographic factors that are relevant to leukemia and other cancers, as well as those relevant to other diseases, disorders, and conditions.

As used herein, the term "environmental factor(s)" are features associated with the surrounding circumstances, objects or conditions. Environmental factors may determine the development of disease in those genetically predisposed to a particular condition. Examples include, but are not limited to, stress, physical abuse, mental abuse, diet, maternal diet, infection, and exposure to carcinogens, toxins, pathogens, teratogens, radiation, or chemicals. In illustrative embodiment, environmental factor related to cancers include, but are not limited to, exposure to carcinogens, exposure to radiation, hormone treatment, diet, stress, exposure to sexually transmitted diseases, and air pollution. In some embodiments, environmental factors associated with leukemia in children include, but are not limited to, ionizing radiation, exposure to benzene, maternal alcohol consumption, and maternal smoking and drug use. A person of ordinary skill in the art will recognize other environmental factors that are relevant to leukemia and other cancers, as well as those relevant to other diseases, disorders, and conditions.

As used herein, "physiological data" refers to information relating to the normal state of a person, patient, or subject. Examples of physiological data include, but are not limited to, heart rate, complete blood picture, blood pressure, blood oxygen saturation, cardiac output, liver function test, vascular activity, temperature, respiration, cardiac, abdominal, or breathing sounds, blood flow, hormonal concentration, enzyme and protein level, neural activity, electroencephalographic activity, and data associated with other electrical, mechanic, sonic, biochemical, or biophysical processes.

In illustrative embodiment, physiological data related to cancers include, but are not limited to, complete blood count, red blood cell count, white blood cell count, hemoglobin, hematocrit, creatinine levels in blood and urine, body temperature, blood oxygen, and hormone levels. In some embodiments, physiological data associated with leukemia include, but are not limited to, blood oxygen, body temperature, white blood cell count, platelet count, cough, breathing, and levels of lactate dehydrogenase, uric acid, and fibrinogen. A person of ordinary skill in the art will recognize other physiological data that are relevant to leukemia and other cancers, as well as that relevant to other diseases, disorders, and conditions.

As used herein, "symptom(s)" refer to physical or psychological manifestations of a disease, disorder or conditions in a person, patient or subject. Symptoms may be subjective and observed by the patient, but not measured. Symptoms depend on the disease, disorder, and condition, and a symptom may be present in more than one condition. The list of symptoms is extensive and those associated with various conditions are well known in the art. In illustrative embodiments, symptoms of cancers, while depending on the particular type involved and the location of the cancerous growth, may include, but are not limited to, weight loss, fatigue, malaise, fever, shortness of breath, enlarged lymph nodes, pain, headaches, bleeding, swelling, or impairment of neurological function. In some embodiments, symptoms associated with cardiovascular diseases include, but are not limited to, pain, shortness of breath, fatigue, nausea, systemic emboli, and palpitations. A person of ordinary skill in the art will recognize other symptoms associated with cancers and cardiovascular diseases, as well as those relevant to other diseases, disorder, and conditions. For example, the International Statistical Classification of Diseases and Related Health Problems 10th Revision (ICD-10) provides a coding of diseases and signs, symptoms, and abnormal findings.

As used herein, "classification tree(s)" are predictive models that assign membership of cases or objects to classes of a categorical dependent variable from their measurements of one or more predictor variables. The classification may be depicted graphically, embodied in one or more predictive algorithms, or both. For example, the classification tree may be illustrated using a tree diagram having multiple nodes (each representing a classification) and branches (representing divisions within a class). In illustrative embodiments, a possible outcome may be depicted by classification in two or more terminal nodes. The classification may also be represented by a mathematical formula that assigns membership in a class according to values of the predictor variables. In some embodiments, values assigned to the variables may be binary (e.g., representing the presence or absence of a diagnostic factor) or continuous (e.g., representing the measurement of physiological data). In some embodiments, the result provided by an algorithm may be a score representative of a prediction, a predicted value, or a range.

There are various statistical methods that may be used to construct a classification tree. These statistical methods include, but are not limited to, "AID," "THAID," "CHAID," "Exhaustive CHAID," "C&RT," "QUEST," "FACT," "FIRM," "GUIDE" and "CRUISE." In illustrative embodiments, given a dataset representative of diagnostic factors of a disease, a classification tree may be used to detect interaction between two or more diagnostic factors and identify those characteristics that are associated with and/or related to the variation in responses.

As used herein, "discriminant analysis" means a statistical method that examines the set of variables or predictors associated with a given subject and uses similarities and differences to assign the subject to a group or class. In illustrative embodiments, discriminant analysis may be used to analyze two or more diagnostic factors in order to determine those that discriminate between subject groups. In some embodiments, discriminant analysis is used to construct a model for predicting a possible outcome, such as prognosis. In illustrative embodiments, the model is optionally used to assign a particular subject to a predicted class based on their prognostic data put into the model.

In illustrative embodiments, discriminant function analysis may be used to determine whether subject groups differ with regard to the mean of a variable, and then to use that variable to further predict group membership. In illustrative embodiments, the analysis provides coefficients for each variable in each discriminant function; the larger the standardized coefficient, the greater is the contribution of the respective variable to the discrimination between groups.

In illustrative embodiments, the factor structure matrix with the correlations between the variables and the discriminant functions is examined to derive substantive and meaningful labels for the discriminant functions. In some embodiments, the means for the significant discriminant functions determine the groups between which the respective functions seem to discriminate.

As used herein, "AID" refers to the computational method known as "Automatic Interaction Detection", which was described by Morgan & Sonquist (1963).

As used herein, "THAID" refers to the computational method known as "Theta Automatic Interaction Detection", which was described by Morgan & Messenger (1973).

As used herein, "CHAID" refers to the computational method known as "Chi-Square Automatic Interaction Detection", which was described by Kass (1980). In illustrative embodiments, CHAID may be used with non-linear or complex datasets in order to find significant patterns and to yield multi-way frequency tables. In illustrative embodiments, possible dependencies in the population are inferred from interactions in the dataset using Chi-squared tests of independence. In illustrative embodiments, the test statistic of the Chi-squared test cumulates the (standardized) squared deviations between observed and expected frequencies, whereby large values of the test statistic indicate interactions between the analyzed variables. In illustrative embodiments, the test statistic is compared to the percentile of the distribution of cumulated, normally distributed random variables to validate the possible dependencies. If the test statistic exceeds the value of this Chi-squared distribution defined by significance level, the null hypothesis of independence of the variables is rejected.

As used herein, "Exhaustive CHAID" refers to the computational method known as "Exhaustive Chi-Square Automatic Interaction Detection", also known as "Modified CHAID", which is based on Biggs, de Ville and Suen (1991).

As used herein, "C&RT" refers to the computational method known as "Classification and Regression Trees", which was developed by Breiman et al. (1984).

As used herein, QUEST refers to the computational method known as "Quick, Unbiased, Efficient Statistical Trees", which was described by Loh and Shih (1997).

As used herein, "FACT" refers to the computational method known as "Fast Algorithm for Classification Trees", developed by Loh and Vanichestakul (1988).

As used herein, "FIRM" refers to the computational method known as "Formal Interference-based Recursive Modeling", which is a collection of codes presented by Hawkins (1990) for the implementation of CHAID.

As used herein, "GUIDE" refers to the computational method known as "Generalized Unbiased Interaction Detection and Estimation", which was proposed by Loh (2002).

As used herein, "CRUISE" refers to the computational method known as "Classification Rule with Unbiased Interaction Selection and Estimation", which was described by Kim and Loh (2001).

In one aspect, the disclosure is drawn to one or more methods for predicting a possible outcome of a multi-factored disease, disorder or condition. Although one or more methods may be presented separately herein, it is intended and envisioned that one or more methods and/or embodiments of one or more methods may be combined and/or substituted to encompass the full disclosure. In some embodiments, one or more methods described herein may be performed on one or more apparatus described herein. In some embodiments, one or more methods may include one or more operations, and using all or more computing devices and/or systems.

In some embodiments, one or more methods include receiving an input, the input representative of one or more diagnostic factors of a multi-factored disease, disorder or condition, and predicting a possible outcome based on the input, wherein predicting a possible outcome based on the input includes constructing a classification tree of two or more diagnostic factors of the multi-factored disease, disorder or condition, and performing discriminant analysis of the two or more diagnostic factors.

In some embodiments, receiving an input includes receiving a first data entry. In some embodiments, receiving an input includes receiving a first data entry from a graphical user interface. In some embodiments, receiving an input includes receiving a first data entry from at least one submission element of a graphical user interface.

In some embodiments, receiving an input includes receiving the input, the input representative of one or more diagnostic factors selected from physical attributes, genetic characteristics, demographic factors, environmental factors, physiological data, and symptoms.

In some embodiments, the one or more diagnostic factors is a physical attribute. In some embodiments, the physical attribute is selected from characteristics associated with height, disease state, body type, vision, strength, coordination, fertility, weight, skin, skeleto-muscular, longevity, and hair.

In some embodiments, at least one of the one or more diagnostic factors is a genetic characteristic. In some embodiments, the genetic characteristic is associated with genes, alleles, chromosomes, DNA, or RNA. In some embodiments, they may relate to gene sequences, mutations, abnormalities, inversions, insertions, deletions, substitutions, duplications, single nucleotide polymorphisms, haplotypes, centromeres, telomeres, methylation patterns, introns, and exons.

In some embodiments, at least one of the one or more diagnostic factors is a demographic factor. In some embodiments, the demographic factor is selected from race, ethnicity, age, sex, education level, income level, marital status, employment status, occupation, religion, location, family size, and exposure profile to environmental factors.

In some embodiments, at least one of the one or more diagnostic factors is an environmental factor. In some embodiments, the environmental factor is selected from stress, physical abuse, mental abuse, diet, maternal diet, infection, and exposure to carcinogens, toxins, pathogens, teratogens, radiation, or chemicals.

In some embodiments, at least one of the one or more diagnostic factors is physiological data. In some embodiments, the physiological data is selected from heart rate, blood pressure, blood oxygen saturation, cardiac output, vascular activity, temperature, respiration, cardiac, abdominal, or breathing sounds, blood flow, hormonal concentration, enzyme and protein level, neural activity, electroencephalographic activity, and data associated with other electrical, mechanic, sonic, biochemical, or biophysical processes.

In some embodiments, at least one of the one or more diagnostic factors is a symptom.

In some embodiments, the multi-factored disease, disorder or condition is selected from cancers, autoimmune diseases, cardiovascular diseases, infectious diseases, endocrinological disorders, developmental abnormalities, mental disorders, neurological disorders, inflammatory disorders, and obesity and eating disorders. In some embodiments, the multi-factored disease, disorder or condition is selected from leukemia; cancers of the bladder, brain, breast, colon, esophagus, kidney, liver, lung, mouth, ovary, pancreas, prostate, skin, stomach and uterus; rheumatoid arthritis; multiple sclerosis; epilepsy; diabetes; osteoporosis; bipolar disorder; schizophrenia; atopy; inflammatory bowel disease; asthma; systemic lupus erythematosus; Grave's disease; angina pectoris; myocardial infarcation; heart disease; cardiomyopathies; dsyrthythmias; AIDS; Lyme disease; bacterial meningitis; bacteremia and sepsis; sexually transmitted diseases; osteomyelitis; brain injuries, Parkinson's disease; Alzheimer's disease; congenital heart defects; neural tube defects; obesity and eating disorders. In some embodiments, the multi-factored disease, disorder or condition is a cancer.

In some embodiments, the possible outcome is selected from a diagnosis, prognosis, possible risk, possible result, possible consequence, likelihood of success, result of a course of treatment, existence or non-existence of a characteristic or feature of the disease, achievement of a milestone, or cost. In some embodiments, the possible outcome is a diagnosis. In some embodiments, the possible outcome is a prognosis. In some embodiments, prognosis is described based on survivability, risk, life expectancy, a scoring system, or terms descriptive of prognosis. For example, a prognosis based on survivability may use classifications including, but not limited to, resistance to treatment, relapse, and disease-free survival. In some embodiments, survivability may be expressed using a probability, such as a 10% chance of survival, a 25% percent change of survival, or an 80% chance of survival. In some embodiments, survivability may be expressed as a probability for a certain period of time, such as a 2-year survival of 75%, 2-year survival of 25%, or 5-year survival of 50%.

In some embodiments, prognosis may refer to a patient's chance of recovery, improvement, survival, etc., such as excellent, good, fair, poor, and very poor. In some embodiments, prognosis may refer to a patient's chance of risk of death, deterioration, metastasis, etc., such as very low risk, low risk, intermediate risk, high risk, and very high risk.

In some embodiments, the possible outcome is the existence or non-existence of a disorder, disorder, or condition or of some feature or characteristic thereof. For example, a patient may be suffering from an unknown condition. Diagnosis of a particular disease, disorder, or condition may be predicted based on an analysis of diagnostic factors. As another illustrative example, it may be desirable to predict whether a particular feature or characteristic of a disease, disorder, or condition (such as pain, infection, and complications) will manifest itself.

In some embodiments, the possible outcome may be the consequence of possible treatments (such as effectiveness or occurrence of side effects). For example, a clinician may be able to determine the most desirable course of treatment based on an analysis of diagnostic factors associated with the patient.

In some embodiments, constructing a classification tree of two or more diagnostic factors of the multi-factored disease, disorder or condition includes constructing the classification tree of two or more diagnostic factors selected from physical attributes, genetic characteristics, demographic factors, environmental factors, physiological data, and symptoms.

In some embodiments, constructing a classification tree of two or more diagnostic factors of the multi-factored disease, disorder or condition includes constructing the classification tree using a computational method selected from AID, THAID, CHAID, Exhaustive CHAID, C&RT, QUEST, FACT, FIRM, GUIDE and CRUISE. In some embodiments, constructing a classification tree of two or more diagnostic factors of the multi-factored disease, disorder or condition includes constructing the classification tree using CHAID.

In some embodiments, one or methods include generating a graphical illustration of at least one of (a) the classification tree of two or more diagnostic factors of the multi-factored disease, disorder or condition, and (b) the discriminant analysis of the two or more diagnostic factors. In some embodiments, the graphical illustration is a tree diagram having multiple nodes (each representing a classification) and branches (representing divisions within a class). In illustrative embodiments, a possible outcome may be depicted by classification in two or more terminal nodes.

In some embodiments, generating a graphical illustration of at least one of (a) the classification tree of two or more diagnostic factors of the multi-factored disease, disorder or condition, and (b) the discriminant analysis of the two or more diagnostic factors includes generating the graphical illustration for inclusion in a display element of a graphical user interface.

In some embodiments, generating a graphical illustration of at least one of (a) the classification tree of two or more diagnostic factors of the multi-factored disease, disorder or condition, and (b) the discriminant analysis of the two or more diagnostic factors includes performing an analysis of at least one of the classification tree and the discriminant analysis, and generating the graphical illustration based on the analysis.

In some embodiments, one or methods include generating a graphical illustration of the possible outcome. In some embodiments, generating a graphical illustration of the possible outcome includes generating the graphical illustration for inclusion in a display element of a graphical user interface. In some embodiments, the graphical illustration may include, but is not limited to, an indication of the prediction of the possible outcome and optionally an indication of the accuracy of the prediction.

In some embodiments, generating a graphical illustration of the possible outcome includes performing an analysis of the input and at least one of (a) the classification tree of two or more diagnostic factors of the multi-factored disease, disorder or condition, and (b) the discriminant analysis of the two or more diagnostic factors, and generating the graphical illustration based on the analysis.

In some embodiments, the one or more methods include generating a mathematical algorithm that assigns membership in a class according to values of the predictor variables. In some embodiments, values assigned to the variables may be binary (e.g., representing the presence or absence of a diagnostic factor) or continuous (e.g., representing the measurement of physiological data). In some embodiments, the result provided by an algorithm may be a score representative of a prediction, a predicted value, or a range.

In illustrative embodiments, the mathematical algorithm includes a discriminant function. In some embodiments, the discriminant function provides a score as a function of discriminant variables, where the score represents membership in a class.

In some embodiments, one or more methods include receiving an input, the input representative of one or more diagnostic factors of a multi-factored disease, disorder or condition, analyzing the input and at least one of (a) a classification tree of two or more diagnostic factors of the multi-factored disease, disorder or condition, and (b) a discriminant analysis of the two or more diagnostic factors, and predicting a possible outcome based on the analysis.

In some embodiments, one or more methods include generating a graphical illustration of the analysis. In some embodiments, generating a graphical illustration of the analysis includes generating the graphical illustration for inclusion in a display element of a graphical user interface.

Figure 2:
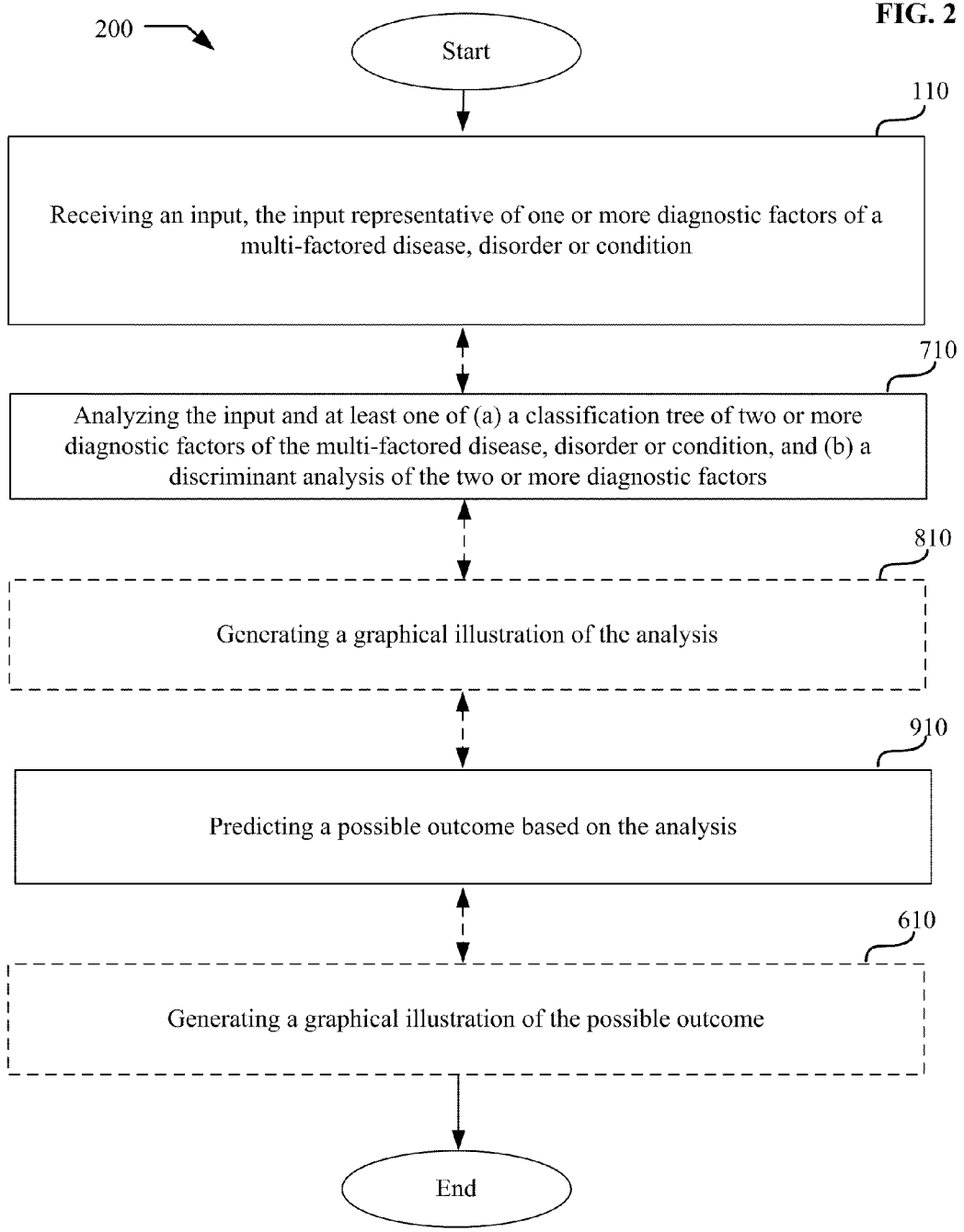

FIG. 1 and FIG. 2 show operational flow 100 and operational flow 200, respectively, representing illustrative embodiments of operations related to determining parameters for selecting one or more reproductive components based on the first possible dataset. In FIG. 1 and FIG. 2, and in the following figures that include various illustrative embodiments of operational flows, discussion and explanation may be provided with respect to apparatus and methods described herein, and/or with respect to other examples and contexts. The operational flows may also be executed in a variety of other contexts and environments, and or in modified versions of those described herein. In addition, although some of the operational flows are presented in sequence, the various operations may be performed in various repetitions, concurrently, and/or in other orders than those that are illustrated.

After a start operation, the operational flows 100 and 200 move to a receiving operation 110, receiving an input representative of one or more diagnostic factors of a multi-factored disease, disorder or condition.

The operational flow 100 moves to operation 210, predicting a possible outcome based on the input. The predicting operation 210 includes operation 310, constructing a classification tree of two or more diagnostic factors of the multi-factored disease, disorder or condition, and operation 410, performing discriminant analysis of the two or more diagnostic factors.

The operational flow 100 optionally moves to generating operation 510, generating a graphical illustration of at least one of (a) the classification tree of two or more diagnostic factors of the multi-factored disease, disorder or condition, and (b) the discriminant analysis of the two or more diagnostic factors. For example, the graphical illustration may include, but is not limited to, a tree diagram having multiple nodes and branches.

The operational flow 200 moves to operation 710, analyzing the input and at least one of (a) a classification tree of two or more diagnostic factors of the multi-factored disease, disorder or condition, and (b) a discriminant analysis of the two or more diagnostic factors. The operational flow 200 optionally moves to a generating operation 810, generating a graphical illustration of the analysis. For example, the graphical illustration may include, but is not limited to, an illustration of a mathematical algorithm that assigns membership in a class according to values of the predictor variables. Then, the operational flow 200 moves to operation 910, predicting a possible outcome based on the analysis.

Then, the operational flows 100 and 200 optionally move to generating operation 610, generating a graphical illustration of the possible outcome. For example, the graphical illustration may include, but is not limited to, an indication of the prediction of the possible outcome and optionally an indication of the accuracy of the prediction.

One or more of operations 110 through 910 may be performed or repeated, as appropriate under the circumstances, prior to an end operation.

Operations 110 to 510 may be performed with respect to a digital representation (e.g. digital data) of, for example, data representative of one or more diagnostic factors. The logic may accept a digital or analog (for conversion into digital) representation of an input and/or provide a digitally-encoded representation of a graphical illustration, where the input may be implemented and/or accessed locally or remotely.

Operations 110 to 910 may be performed related to either a local or a remote storage of the digital data, or to another type of transmission of the digital data. In addition to inputting, accessing querying, recalling, calculating, determining or otherwise obtaining the digital data, operations may be performed related to storing, assigning, associating, displaying or otherwise archiving the digital data to a memory, including for example, sending and/or receiving a transmission of the digital data from a remote memory. Accordingly, any such operations may involve elements including at least an operator (e.g. human or computer) directing the operation, a transmitting computer, and/or receiving computer, and should be understood to occur in the United States as long as at least one of these elements resides in the United States.

Figure 3:
FIG. 3 shows optional embodiments of the operational flow of FIG. 1 and/or FIG. 2.
Figure 4:
FIG. 4 shows optional embodiments of the operational flow of FIG. 1 and/or FIG. 2.

FIG. 3, FIG. 4, FIG. 5, FIG. 6, FIG. 7, FIG. 8 and FIG. 9 illustrate optional embodiments of the operational flows 100 and/or 200 of FIG. 1 and FIG. 2, respectively. FIG. 3 and FIG. 4 show illustrative embodiments of the receiving operation 110, receiving an input representative of one or more diagnostic factors of a multi-factored disease, disorder or condition. Receiving operations may optionally include, but are not limited to, operation 1100, operation 1101, operation 1102, operation 1103, operation 1104, operation 1105, operation 1106, operation 1107, operation 1108, operation 1109, operation 1110, operation 1111, and/or operation 1112.

At the optional operation 1100, receiving an input representative of one or more diagnostic factors comprises receiving a first data entry. At the optional operation 1101, receiving an input representative of one or more diagnostic factors comprises receiving a first data entry from a graphical user interface. At the optional operation 1102, receiving an input representative of one or more diagnostic factors comprises receiving a first data entry from at least submission element of a graphical user interface. In some embodiments, the user is prompted to enter a first data entry corresponding to information associated with one or more diagnostic factors.

At the optional operation 1103, receiving an input representative of one or more diagnostic factors comprises receiving the input, the input representative of one or more diagnostic factors selected from physical attributes, genetic characteristics, demographic factors, environmental factors, physiological data, and symptoms. In some embodiments, the input is representative of one or more genetic characteristics. In some embodiments, the input is representative of one or more genetic characteristics and one or more other diagnostic factors selected from physical attributes, demographic factors, environmental factors, physiological data, and symptoms.

At the optional operation 1104, receiving an input representative of one or more diagnostic factors comprises receiving the input, the input representative of one or more diagnostic factors selected from physical attributes, genetic characteristics, demographic factors, environmental factors, physiological data, and symptoms, wherein at least one of the diagnostic factors is a physical attribute. In some embodiments, the physical attribute is selected from characteristics associated with height, disease state, body type, vision, strength, coordination, fertility, weight, skin, skeleto-muscular, longevity, and hair.

At the optional operation 1105, receiving an input representative of one or more diagnostic factors comprises receiving the input, the input representative of one or more diagnostic factors selected from physical attributes, genetic characteristics, demographic factors, environmental factors, physiological data, and symptoms, wherein at least one of the diagnostic factors is a genetic characteristic. In some embodiments, the genetic characteristic is associated with genes, alleles, chromosomes, DNA, or RNA. In some embodiments, they may relate to gene sequences, mutations, abnormalities, inversions, insertions, deletions, substitutions, duplications, single nucleotide polymorphisms, haplotypes, centromeres, telomeres, methylation patterns, introns, and exons.

At the optional operation 1106, receiving an input representative of one or more diagnostic factors comprises receiving the input, the input representative of one or more diagnostic factors selected from physical attributes, genetic characteristics, demographic factors, environmental factors, physiological data, and symptoms, wherein at least one of the diagnostic factors is a demographic factor. In some embodiments, the demographic factor is selected from race, ethnicity, age, sex, education level, income level, marital status, employment status, occupation, religion, location, family size, and exposure profile to environmental factors.

At the optional operation 1107, receiving an input representative of one or more diagnostic factors comprises receiving the input, the input representative of one or more diagnostic factors selected from physical attributes, genetic characteristics, demographic factors, environmental factors, physiological data, and symptoms, wherein at least one of the diagnostic factors is an environmental factor. In some embodiments, the environmental factor is selected from stress, physical abuse, mental abuse, diet, maternal diet, infection, and exposure to carcinogens, toxins, pathogens, teratogens, radiation, or chemicals.

At the optional operation 1108, receiving an input representative of one or more diagnostic factors comprises receiving the input, the input representative of one or more diagnostic factors selected from physical attributes, genetic characteristics, demographic factors, environmental factors, physiological data, and symptoms, wherein at least one of the diagnostic factors is physiological data. In some embodiments, heart rate, blood pressure, blood oxygen saturation, cardiac output, vascular activity, temperature, respiration, cardiac, abdominal, or breathing sounds, blood flow, hormonal concentration, enzyme and protein level, neural activity, electroencephalographic activity, and data associated with other electrical, mechanic, sonic, biochemical, or biophysical processes.

At the optional operation 1109, receiving an input representative of one or more diagnostic factors comprises receiving the input, the input representative of one or more diagnostic factors selected from physical attributes, genetic characteristics, demographic factors, environmental factors, physiological data, and symptoms, wherein at least one of the diagnostic factors is a symptom. In some embodiments, the symptom is selected from weight loss, fatigue, malaise, fever, shortness of breath, enlarged lymph nodes, pain, headaches, bleeding, swelling, impairment of neurological function, pain, nausea, systemic emboli, and palpitations.

At the optional operation 1110, receiving an input representative of one or more diagnostic factors comprises receiving an input representative of one or more diagnostic factors of a multi-factored disease, disorder, or condition, where the multi-factored disease, disorder, or condition is selected from cancers, autoimmune diseases, cardiovascular diseases, infectious diseases, endocrinological disorders, developmental abnormalities, mental disorders, neurological disorders, inflammatory disorders, and obesity and eating disorders.

At the optional operation 1111, receiving an input representative of one or more diagnostic factors comprises receiving an input representative of one or more diagnostic factors of a multi-factored disease, disorder, or condition, where the multi-factored disease, disorder, or condition is selected from leukemia; cancers of the bladder, brain, breast, colon, esophagus, kidney, liver, lung, mouth, ovary, pancreas, prostate, skin, stomach and uterus; rheumatoid arthritis; multiple sclerosis; epilepsy; diabetes; osteoporosis; bipolar disorder; schizophrenia; atopy; inflammatory bowel disease; asthma; systemic lupus erythematosus; Grave's disease; angina pectoris; myocardial infarcation; heart disease; cardiomyopathies; dsyrthythmias; AIDS; Lyme disease; bacterial meningitis; bacteremia and sepsis; sexually transmitted diseases; osteomyelitis; brain injuries, Parkinson's disease; Alzheimer's disease; congenital heart defects; neural tube defects; obesity and eating disorders.

At the optional operation 1112, receiving an input representative of one or more diagnostic factors comprises receiving an input representative of one or more diagnostic factors of a multi-factored disease, disorder, or condition, where the multi-factored disease, disorder, or condition is a cancer. In some embodiments, the multi-factored disease, disorder, or condition is leukemia. In some embodiment, the multi-factored disease, disorder, or condition is acute lymphocytic leukemia.

Figure 5:
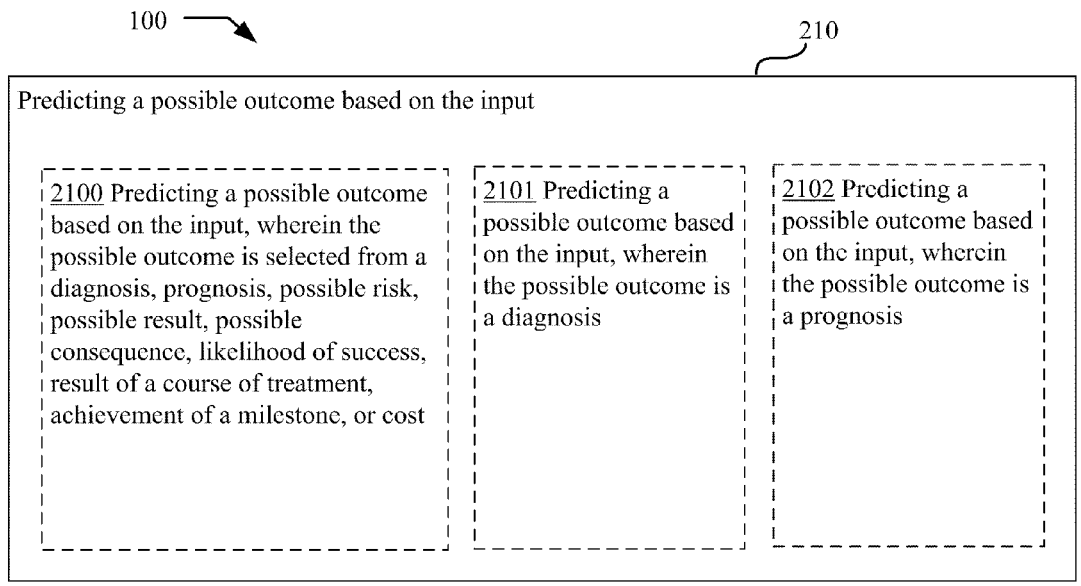
FIG. 5 shows optional embodiments of the operational flow of FIG. 1 and/or FIG. 2.

FIG. 5 shows illustrative embodiments of operation 210, predicting a possible outcome based on the input. Optional operations include, but are not limited to, operation 2100, operation 2101, and/or operation 2102.

At the optional operation 2100, predicting a possible outcome based on the input, comprises predicting a possible outcome, where the possible outcome is selected from a diagnosis, prognosis, possible risk, possible result, possible consequence, likelihood of success, result of a course of treatment, existence or non-existence of a characteristic or feature of the disease, achievement of a milestone, or cost. At the optional operation 2101, predicting a possible outcome based on the input, comprises predicting a possible outcome, where the possible outcome is a diagnosis. At the optional operation 2102, predicting a possible outcome based on the input, comprises predicting a possible outcome, where the possible outcome is a prognosis.

Figure 6:
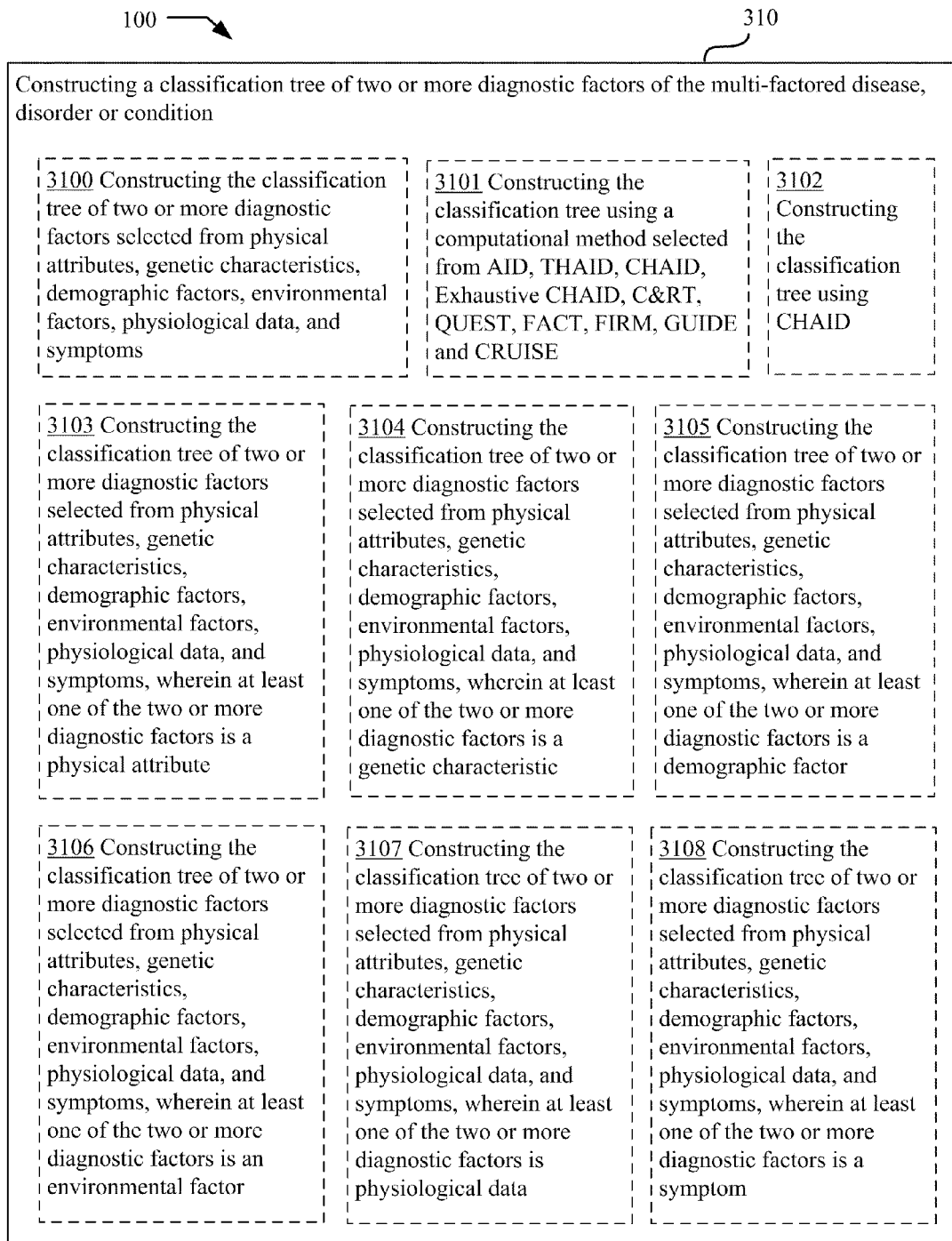
FIG. 6 shows optional embodiments of the operational flow of FIG. 1 and/or FIG. 2.

FIG. 6 shows illustrative embodiments of operation 310, constructing a classification tree of two or more diagnostic factors of the multi-factored disease, disorder or condition. Optional operations include, but are not limited to, operation 3100, operation 3101, operation 3102, operation 3103, operation 3104, operation 3105, operation 3106, operation 3107, and/or operation 3108.

At the optional operation 3100, constructing a classification tree of two or more diagnostic factors of the multi-factored disease, disorder or condition comprises constructing the classification tree of two or more diagnostic factors selected from physical attributes, genetic characteristics, demographic factors, environmental factors, physiological data, and symptoms.

At the optional operation 3101, constructing a classification tree of two or more diagnostic factors of the multi-factored disease, disorder or condition comprises constructing the classification tree using a computational method selected from AID, THAID, CHAID, Exhaustive CHAID, C&RT, QUEST, FACT, FIRM, GUIDE and CRUISE. At the optional operation 3102, constructing a classification tree of two or more diagnostic factors of the multi-factored disease, disorder or condition comprises constructing the classification tree using CHAID.

At the optional operations 3103, 3104, 3105, 3106, 3107, and 3108, constructing a classification tree of two or more diagnostic factors of the multi-factored disease, disorder or condition comprises constructing the classification tree of two or more diagnostic factors where at least one of the two or more diagnostic factors are, respectively, a physical attribute, genetic characteristic, demographic factor, environmental factor, physiological data, or symptom.

FIG. 7 shows illustrative embodiments of operation 510, generating a graphical illustration of at least one of (a) the classification tree of two or more diagnostic factors of the multi-factored disease, disorder or condition, and (b) the discriminant analysis of the two or more diagnostic factors. Optional operations include, but are not limited to, operation 5100, operation 5101, and/or operation 5102.

At the optional operation 5100, generating a graphical illustration of at least one of (a) the classification tree of two or more diagnostic factors of the multi-factored disease, disorder or condition, and (b) the discriminant analysis of the two or more diagnostic factors comprises generating the graphical illustration for inclusion in a display element of a graphical user interface.

At the optional operation 5101, generating a graphical illustration of at least one of (a) the classification tree of two or more diagnostic factors of the multi-factored disease, disorder or condition, and (b) the discriminant analysis of the two or more diagnostic factors comprises performing an analysis of at least one of the classification tree and the discriminant analysis. Then, at the optional operation 5102, the graphical illustration is generated based on the analysis.

Figure 8:
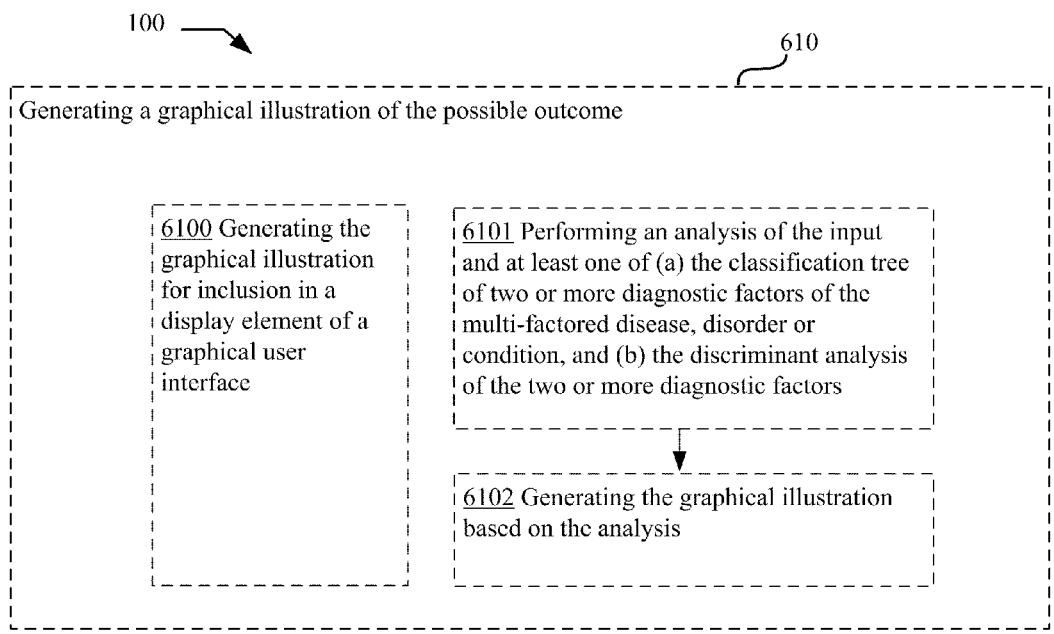
FIG. 8 shows optional embodiments of the operational flow of FIG. 1 and/or FIG. 2.

FIG. 8 shows illustrative embodiments of operation 610, generating a graphical illustration of the possible outcome. Optional operations include, but are not limited to, operation 6100, operation 6101, and/or operation 6102.

At optional operation 6100, generating a graphical illustration of the possible outcome comprises generating the graphical illustration for inclusion in a display element of a graphical user interface. At optional operation 6101, generating a graphical illustration of the possible outcome comprises performing an analysis of the input and at least one of (a) the classification tree of two or more diagnostic factors of the multi-factored disease, disorder or condition, and (b) the discriminant analysis of the two or more diagnostic factors. Then, at optional operation 6102, the graphical illustration is generated based on the analysis.

Figure 9:
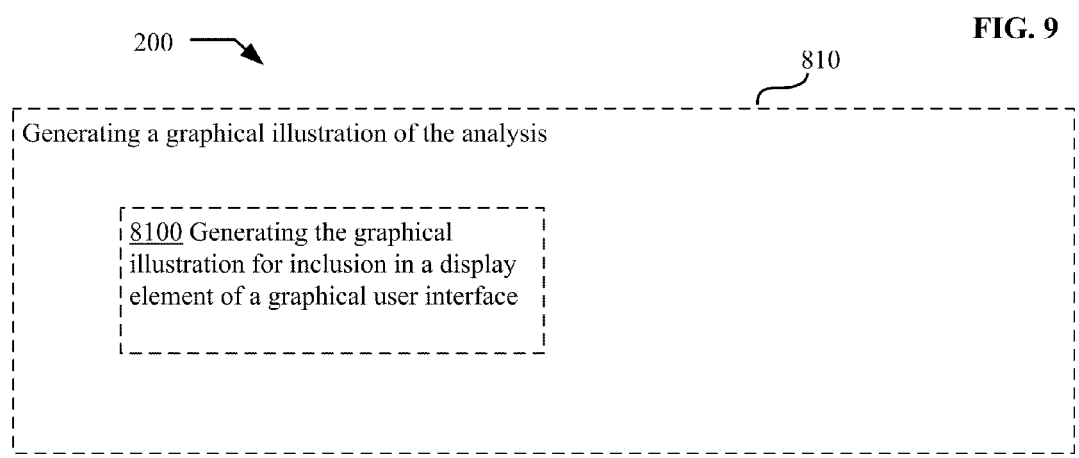
FIG. 9 shows optional embodiments of the operational flow of FIG. 1 and/or FIG. 2.

FIG. 9 shows illustrative embodiments of operation 810, generating a graphical illustration of the analysis. Optional operations include, but are not limited to, operation 8100. At optional operation 8100, generating a graphical illustration of the analysis comprises generating the graphical illustration for inclusion in a display element of a graphical user interface.

In one aspect, the disclosure is drawn to one or more computer program products including a signal bearing medium bearing at least one of one or more instructions for receiving an input, the input representative of one or more diagnostic factors of a multi-factored disease, disorder or condition; and one or more instructions for predicting a possible outcome based on the input, wherein the one or more instructions for predicting a possible outcome based on the input include one or more instructions for constructing a classification tree of two or more diagnostic factors of the multi-factored disease, disorder or condition, and one or more instructions for performing discriminant analysis of the two or more diagnostic factors.

In some embodiments, the signal bearing medium includes a computer-readable medium. In some embodiments, the signal bearing medium includes a recordable medium. In some embodiments, the signal bearing medium includes a communications medium.

In some embodiments, the one or more instructions for constructing a classification tree of two or more diagnostic factors of the multi-factored disease, disorder or condition include one or more instructions for constructing the classification tree using a computational method selected from AID, THAID, CHAID, Exhaustive CHAID, C&RT, QUEST, FACT, FIRM, GUIDE and CRUISE. In some embodiments, the one or more instructions for constructing a classification tree of two or more diagnostic factors of the multi-factored disease, disorder or condition include one or more instructions for constructing the classification tree using CHAID.

In some embodiments, one or more computer program products include one or more instructions for generating a graphical illustration of at least one of (a) the classification tree of two or more diagnostic factors of the multi-factored disease, disorder or condition, and (b) the discriminant analysis of the two or more diagnostic factors.

In some embodiments, the one or more instructions for generating a graphical illustration of at least one of (a) the classification tree of two or more diagnostic factors of the multi-factored disease, disorder or condition, and (b) the discriminant analysis of the two or more diagnostic factors include one or more instructions for generating the graphical illustration for inclusion in a display element of a graphical user interface.

In some embodiments, the one or more instructions for generating a graphical illustration of at least one of (a) the classification tree of two or more diagnostic factors of the multi-factored disease, disorder or condition, and (b) the discriminant analysis of the two or more diagnostic factors include one or more instructions for performing an analysis of at least one of the classification tree and the discriminant analysis, and one or more instructions for generating the graphical illustration based on the analysis.

In some embodiments, one or more computer program products include one or more instructions for generating a graphical illustration of the possible outcome. In some embodiments, the one or more instructions for generating a graphical illustration of the possible outcome include one or more instructions for generating the graphical illustration for inclusion in a display element of a graphical user interface.

In some embodiments, the one or more instructions for generating a graphical illustration of the possible outcome include one or more instructions for performing an analysis of the input and at least one of (a) the classification tree of two or more diagnostic factors of the multi-factored disease, disorder or condition, and (b) the discriminant analysis of the two or more diagnostic factors; and one or more instructions for generating the graphical illustration based on the analysis.

In some embodiments, one or more computer program products include a signal bearing medium bearing at least one of one or more instructions for receiving an input, the input representative of one or more diagnostic factors of a multi-factored disease, disorder or condition; one or more instructions for analyzing the input and at least one of (a) a classification tree of two or more diagnostic factors of the multi-factored disease, disorder or condition, and (b) a discriminant analysis of the two or more diagnostic factors; and one or more instructions for predicting a possible outcome based on the analysis.

In some embodiments, one or more computer program products include one or more instructions for generating a graphical illustration of the analysis. In some embodiments, the one or more instructions for generating a graphical illustration of the analysis include one or more instructions for generating the graphical illustration for inclusion in a display element of a graphical user interface.

FIG. 10 shows a schematic of a partial view of an illustrative computer program product 1000 that includes a computer program for executing a computer process on a computing device. An illustrative embodiment of the example computer program product is provided using a signal bearing medium 1002, and may include at least one instruction of 1004: one or more instructions for receiving an input representative of one or more diagnostic factors of a multi-factored disease, disorder or condition; and one or more instructions for predicting a possible outcome based on the input, wherein the one or more instructions for predicting a possible outcome based on the input include one or more instructions for constructing a classification tree of two or more diagnostic factors of the multi-factored disease, disorder or condition, and one or more instructions for performing discriminant analysis of the two or more diagnostic factors. The one or more instructions may be, for example, computer executable and/or logic implemented instructions. In some embodiments, the signal bearing medium 1002 of the one or more computer program 1000 products include a computer readable medium 1006, a recordable medium 1008, and/or a communications medium 1010.

Figure 11:
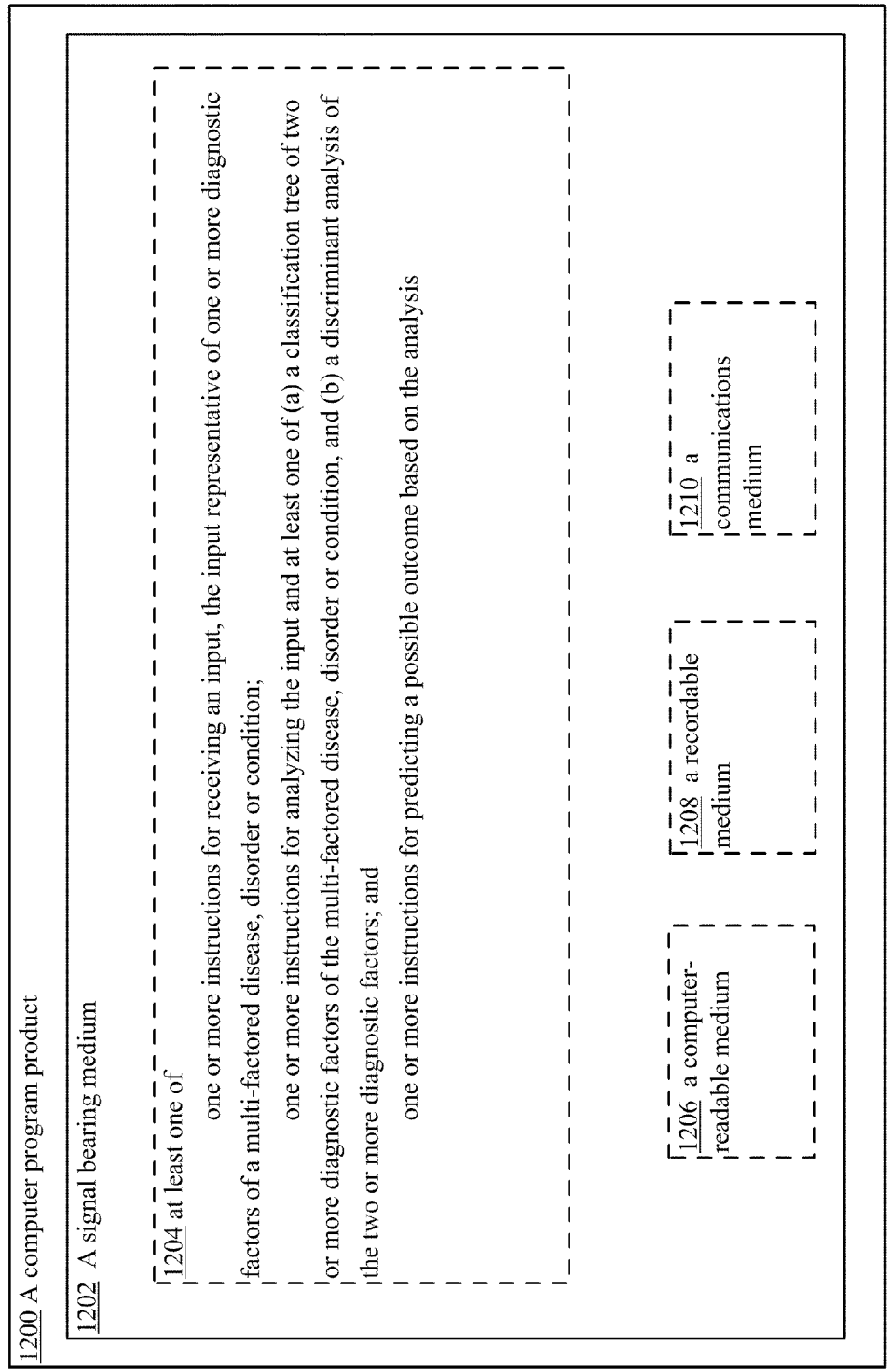

FIG. 11 shows a schematic of a partial view of an illustrative computer program product 1200 that includes a computer program for executing a computer process on a computing device. An illustrative embodiment of the example computer program product is provided using a signal bearing medium 1202, and may include at least one instruction of 1204: one or more instructions for receiving an input, the input representative of one or more diagnostic factors of a multi-factored disease, disorder or condition; one or more instructions for analyzing the input and at least one of (a) a classification tree of two or more diagnostic factors of the multi-factored disease, disorder or condition, and (b) a discriminant analysis of the two or more diagnostic factors; and one or more instructions for predicting a possible outcome based on the analysis. The one or more instructions may be, for example, computer executable and/or logic implemented instructions. In some embodiments, the signal bearing medium 1202 of the one or more computer program 1200 products include a computer readable medium 1006, a recordable medium 1208, and/or a communications medium 1210.

In one aspect, the disclosure is drawn to one or more systems including a computing device, and instructions that when executed on the computing device cause the computing device to receive an input, the input representative of one or more diagnostic factors of a multi-factored disease, disorder or condition; and predict a possible outcome based on the input, wherein the prediction of a possible outcome based on the input includes instructions that when executed on the computing device cause the computing device to construct a classification tree of two or more diagnostic factors of the multi-factored disease, disorder or condition; and perform a discriminant analysis of the two or more diagnostic factors.

In some embodiments, the instructions that when executed on the computing device cause the computing device to construct a classification tree of two or more diagnostic factors of the multi-factored disease, disorder or condition include instructions that when executed on the computing device cause the computing device to construct a classification tree using a computational method selected from AID, THAID, CHAID, Exhaustive CHAID, C&RT, QUEST, FACT, FIRM, GUIDE and CRUISE.

In some embodiments, the instructions that when executed on the computing device cause the computing device to construct a classification tree of two or more diagnostic factors of the multi-factored disease, disorder or condition include instructions that when executed on the computing device cause the computing device to construct a classification tree using CHAID.

In some embodiments, one or more systems include instructions that when executed on the computing device cause the computing device to determine a graphical illustration of at least one of (a) the classification tree of two or more diagnostic factors of the multi-factored disease, disorder or condition, and (b) the discriminant analysis of the two or more diagnostic factors.

In some embodiments, the instructions that when executed on the computing device cause the computing device to determine a graphical illustration of at least one of (a) the classification tree of two or more diagnostic factors of the multi-factored disease, disorder or condition, and (b) the discriminant analysis of the two or more diagnostic factors include instructions that when executed on the computing device cause the computing device to determine the graphical illustration for inclusion in a display element of a graphical user interface.

In some embodiments, the instructions that when executed on the computing device cause the computing device to determine a graphical illustration of at least one of (a) the classification tree of two or more diagnostic factors of the multi-factored disease, disorder or condition, and (b) the discriminant analysis of the two or more diagnostic factors include instructions that when executed on the computing device cause the computing device to perform an analysis of at least one of the classification tree and the discriminant analysis, and instructions that when executed on the computing device cause the computing device to generate the graphical illustration based on the analysis.

In some embodiments, one or more systems include instructions that when executed on the computing device cause the computing device to determine a graphical illustration of the possible outcome. In some embodiments, the instructions that when executed on the computing device cause the computing device to determine a graphical illustration of the possible outcome include instructions that when executed on the computing device cause the computing device to determine the graphical illustration for inclusion in a display element of a graphical user interface.

In some embodiments, the instructions that when executed on the computing device cause the computing device to determine a graphical illustration of the possible outcome include instructions that when executed on the computing device cause the computing device to perform an analysis of the input and at least one of (a) the classification tree of two or more diagnostic factors of the multi-factored disease, disorder or condition, and (b) the discriminant analysis of the two or more diagnostic factors, and instructions that when executed on the computing device cause the computing device to generate the graphical illustration based on the analysis.

In some embodiments, one or more systems include one or more of a desktop computer, a workstation computer, a computing system comprised of a cluster of processors, a networked computer, a tablet personal computer, a laptop computer, a personal digital assistant, a smartphone, or a mobile computing device.

In some embodiments, one or more systems include a computing device, and instructions that when executed on the computing device cause the computing device to receive an input, the input representative of one or more diagnostic factors of a multi-factored disease, disorder or condition; analyze the input and at least one of (a) a classification tree of two or more diagnostic factors of the multi-factored disease, disorder or condition, and (b) a discriminant analysis of the two or more diagnostic factors; and predict a possible outcome based on the analysis.

In some embodiments, the instructions that when executed on the computing device cause the computing device to generate a graphical illustration of the analysis include instructions that when executed on the computing device cause the computing device to generate the graphical illustration for inclusion in a display element of a graphical user interface.

In some embodiments, one or more systems include instructions that when executed on the computing device cause the computing device to generate a graphical illustration of the analysis. In some embodiments, the instructions that when executed on the computing device cause the computing device to generate a graphical illustration of the analysis include instructions that when executed on the computing device cause the computing device to generate the graphical illustration for inclusion in a display element of a graphical user interface.

Figure 12:
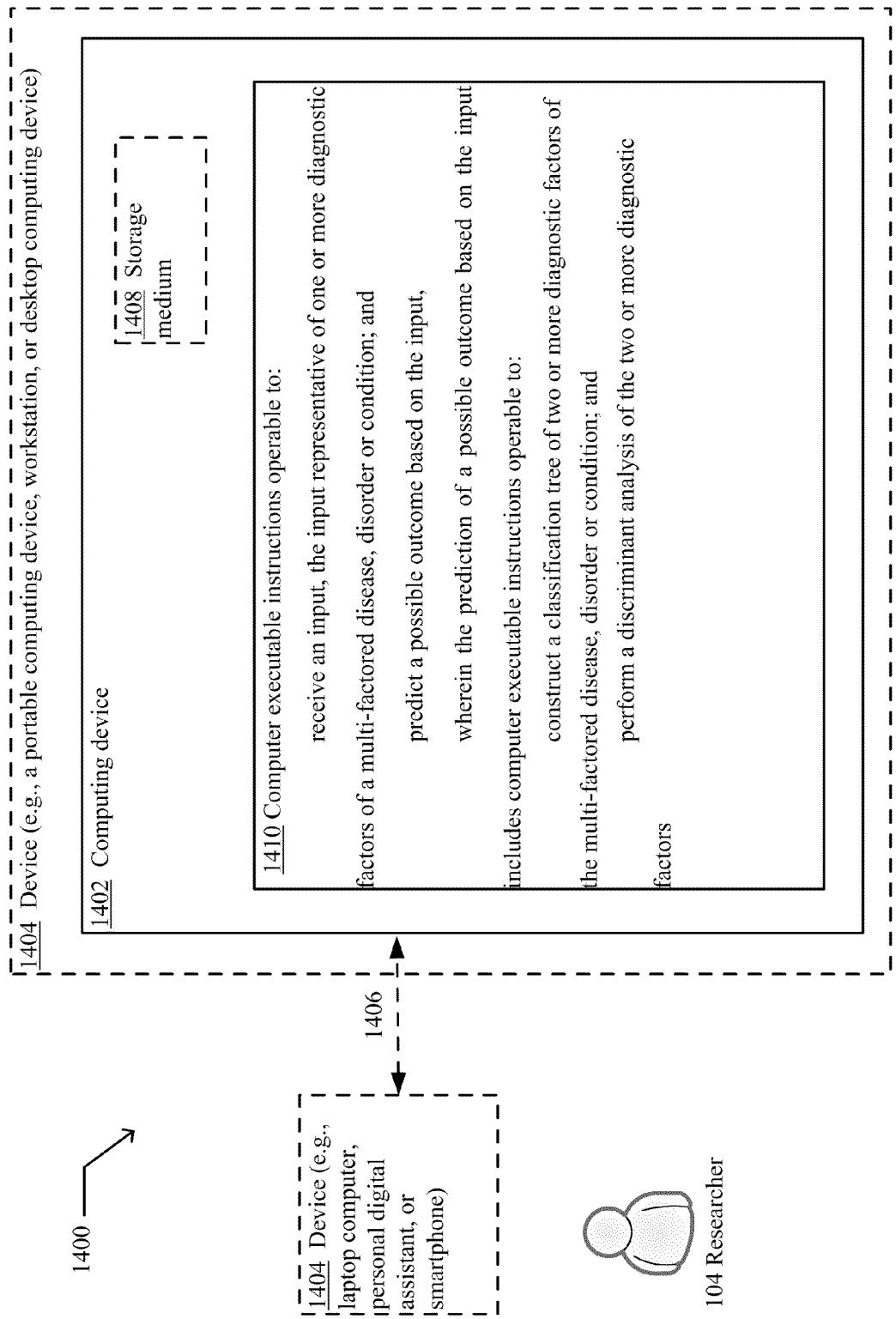
FIG. 12 and FIG. 13 shows an illustrative embodiments of systems in which embodiments may be implemented.

FIG. 12 shows an illustrative embodiment of a system 1400 in which embodiments may be implemented. The system 1400 may include a computing system environment. The system 1400 also illustrates a researcher/scientist/investigator/operator 104 using a device 1404, that is optionally shown as being in communication with a computing device 1402 by way of an optional coupling 1406. The optional coupling may represent a local, wide area, or peer-to-peer network, or may represent a bus that is internal to a computing device (e.g. in illustrative embodiments the computing device 1402 is contained in whole or in part within the device. An optional storage medium 1408 may be any computer storage medium.

The computing device 1402 includes one or more computer executable instructions 1410 that when executed on the computing device 1402 cause the computing device 1402 to receive an input, the input representative of one or more diagnostic factors of a multi-factored disease, disorder or condition; and predict a possible outcome based on the input, wherein the prediction of a possible outcome based on the input includes instructions that when executed on the computing device cause the computing device to construct a classification tree of two or more diagnostic factors of the multi-factored disease, disorder or condition; and perform a discriminant analysis of the two or more diagnostic factors.

The system 1400 includes at least one computing device (e.g. 1404 and/or 1402) on which the computer-executable instructions 1410 may be executed. For example, one or more of the computing devices (e.g. 1402 or 1404) may execute the one or more computer executable instructions 1410 and output a result and/or receive information from the researcher on the same or a different computing device (e.g. 1402 or 1404) and/or output a result in order to perform and/or implement one or more of the techniques, processes, or methods described herein, or other techniques.

The computing device (e.g. 1402 or 1404) may include one or more of a desktop computer, a workstation computer, a computing system comprised a cluster of processors, a networked computer, a tablet personal computer, a laptop computer, or a personal digital assistant, or any other suitable computing unit, such as a smartphone.

Figure 13:
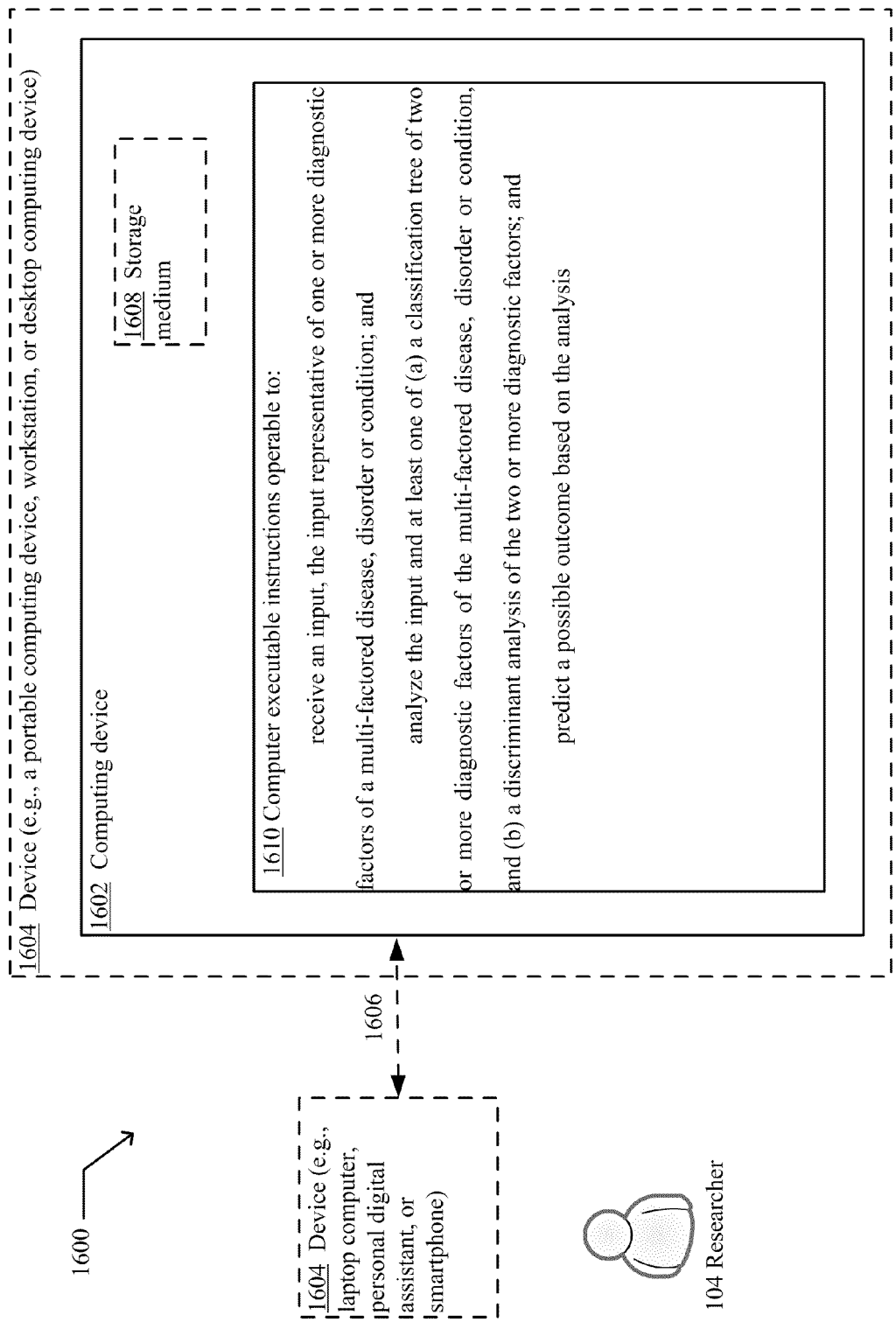

FIG. 13 shows an illustrative embodiment of a system 1600 in which embodiments may be implemented. The system 1600 may include a computing system environment. The system 1600 also illustrates a researcher/scientist/investigator/operator 104 using a device 1604, that is optionally shown as being in communication with a computing device 1602 by way of an optional coupling 1606. The optional coupling may represent a local, wide area, or peer-to-peer network, or may represent a bus that is internal to a computing device (e.g. in illustrative embodiments the computing device 1602 is contained in whole or in part within the device. An optional storage medium 1608 may be any computer storage medium.

The computing device 1602 includes one or more computer executable instructions 1610 that when executed on the computing device 1602 cause the computing device 1602 to receive an input, the input representative of one or more diagnostic factors of a multi-factored disease, disorder or condition; analyze the input and at least one of (a) a classification tree of two or more diagnostic factors of the multi-factored disease, disorder or condition, and (b) a discriminant analysis of the two or more diagnostic factors; and predict a possible outcome based on the analysis.

The system 1600 includes at least one computing device (e.g. 1604 and/or 1602) on which the computer-executable instructions 1610 may be executed. For example, one or more of the computing devices (e.g. 1602 or 1604) may execute the one or more computer executable instructions 1610 and output a result and/or receive information from the researcher on the same or a different computing device (e.g. 1602 or 1604) and/or output a result in order to perform and/or implement one or more of the techniques, processes, or methods described herein, or other techniques.

The computing device (e.g. 1602 or 1604) may include one or more of a desktop computer, a workstation computer, a computing system comprised a cluster of processors, a networked computer, a tablet personal computer, a laptop computer, or a personal digital assistant, or any other suitable computing unit, such as a smartphone.

EXAMPLES

Example 1

Illustrative Cancer Model

One illustrative embodiment relates to methods for predicting possible outcomes in multi-factored diseases, such as cancers. Cancers develop from uncontrolled multiplication of cells. Most cancers are life threatening. Although effective treatment modalities have been developed in a few cases, many cancers remain refractory to currently available therapies. Acute lymphocytic (or lymphoblastic) leukemia ("ALL") is one such cancer and may be used as an illustrative model, although the methods described herein also apply to other cancers and other multi-factored diseases, disorders or conditions.

Leukemia is a malignant condition of white blood cells in which bone marrow is diffusely replaced by relatively immature white blood cells which generally also appear, in large numbers, in the circulating blood. See Robbins and Angell, Basic Pathology, Second Edition, W. B. Saunders Co., Philadelphia, 349-354 (1976). Leukemias may be classified as acute lymphocytic (or lymphoblastic), chronic lymphocytic, acute myelogenous, or chronic myelogenous.

ALL accounts for about 20 percent of all leukemias. In the United States alone, it is diagnosed in approximately 3,000-4,000 patients per year, the majority of whom are children. Risk-associated factors include high white blood count (WBC), certain cytogenetic abnormalities such as Ph+ ALL or t(4:11) and t(1:19), and a slow response to induction chemotherapy. Untreated, the prognosis for survival is approximately four months.

Although several prognostic factors have been identified for children with ALL (Crist W M et al., 1986; Ribeiro R C et al., 1993) and adults with ALL (Hoelzer D et al., 1988; Baccarani M et al., 1982), mechanisms for assessing the holistic impact of the factors on cancer prognosis and outcome are needed. Some of the better-defined prognostic factors include, but are not limited to, age, white blood ("WBC") count, and various cytogenetic characteristics and abnormalities. Other variables related to ALL include genetic polymorphism of genes like glutathione S-transferase enzymes (GSTM1 and GSTT1), some drug metabolizing enzymes like Methylenetetra-hydrofolate reductase (MTHFR), Dihydropyrimidine Dehydrogenase (DPD) and apoptotic gene-Folin like Tyrosine Kinase (FLT3).

A study group consisting of 135 children, ages 1-10 (mean=4.2 years), who were diagnosed with ALL was examined using one or more of the analyses described herein. The patients were categorized into three groups according to the FAB classification (84% (n=113) of the cases had an L1 morphology, L2 subtype was 14% (n=19) and L3 subtype was 2%). Data regarding age, gender, disease characteristics, response and survival were obtained. The data is shown in Table 1.

TABLE: 1

Patient's characteristics at the presentation

|  | No. of Cases (%) |
|---|---|
| Gender | |
| Male | 87 (64.44%) |
| Female | 48 (35.36%) |
| FAB Subtype | |
| L1 | 112 (82.96%) |
| L2 | 19 (14.07%) |
| L3 | 4 (2.96%) |
| Cytogenetics | |
| Normal | 91 (67.4%) |
| Karyotype | 6 (4.44%) |
| t(9; 22) | 2 (1.48%) |
| Philadelphia | 4 (2.96%) |
| inv(16) | 3 (2.22%) |
| Trisomy 8 | 3 (2.22%) |
| Trisomy 21 | 15 (11.1%) |
| Hypodiploidy | 11 (8.15%) |
| Hyperdiploidy | |
| Others | |

Genotypes of the GST M1, GST T1, MTHFR exon 4, MTHFR exon 7, DPD exon 14 and FLT3/ITD were analyzed and are tabulated in Table 2 below. The GST genes were amplified with specific primers by using β-globulin as an internal control. Both multiplex PCR and independent PCR were performed for the GST M1 and GST T1. The GST M1 gave 210 bp fragment, GST T1 was 473 bp and the internal control β-globulin yielded 131 bp fragment. The null genotype frequency obtained was 15.5% for GST T1. The deletion frequency of GSTM1 was 44.44%.

MTHFR C677T and A1298C were screened for individual genotypic characters. The frequency of MTHFR C677C, C677T, and T677T genotypes were 37.77%, 57.03%, and 5.18%. Frequencies of MTHFR A1298A, A1298C, and C1298C genotypes were 30.37%, 61.48%, and 8.14%.

The DPD IVS14+1G>A genotypes were screened by PCR-RFLP. The wild type allele gave a 409 bp band, the heterozygous mutant allele gave 278 bp and 131 bp bands, and the homozygous mutant allele gave 409 bp, 238 bp and 131 bp bands. The analysis showed IVS14+1G>A heterozygous mutations in 9% of cases, and IVS14+1G>A homozygous mutations in 2% of cases. The frequency of DPD IVS14+1G>A mutations in blood samples was also analyzed. The results are shown in Table 2.

Specific primers were used for the amplification of Exon 14 and its flanking intron sequence. Our analysis showed that the patients were heterozygous and homozygous for IVS14+1G>A mutation which changes invariant splice site G-A.

The FLT3 gene was amplified using specific primers for ITD mutations. ITD mutations were evidenced by the presence of abbarent band migrations compared to the control. The bands of the mutant and wild type were captured and evaluated by DNR bio imaging. The ratio of mutant/wild type was detected in 12 out of 135.

The genotyping protocol for the detection of the MTHFR polymorphism was adapted from Frosst et al., for GST was adopted from Tomoki Naoe et al, for FLT3/ITD was adopted from Jens Tiesmeiera et al (2004) and the DPD genotyping protocol was adopted by Van Kuilenburg et al (2002).

TABLE 2

Distribution of genotypes

| Genotype | Patients n = 135 (%) |
|---|---|
| GST M1 Present | 75 (55.55) |
| GST M1 Null | 60 (44.44) |
| GST T1 Present | 87 (64.44) |
| GST T1 Null | 48 (35.55) |
| MTHFR 677CC | 51 (37.77) |
| MTHFR 677CT | 77 (57.03) |
| MTHFR 677TT | 7 (05.18) |
| MTHFR 677CT + TT | 84 (62.22) |
| MTHFR 1298AA | 41 (30.37) |
| MTHFR 1298AC | 83 (61.48) |
| MTHFR 1298CC | 11 (08.14) |
| MTHFR1298AC + CC | 94 (69.62) |
| DPD Exon 14−/− | 120 (88.8) |
| DPD Exon 14+/− | 12 (08.8) |
| DPD Exon 14+/+ | 3 (02.2) |
| FLT3 Negative | 78 (57.7) |
| FLT3 Positive | 57 (42.2) |
| FLT3/ITD | 12 (8.9) |

Figure 14:
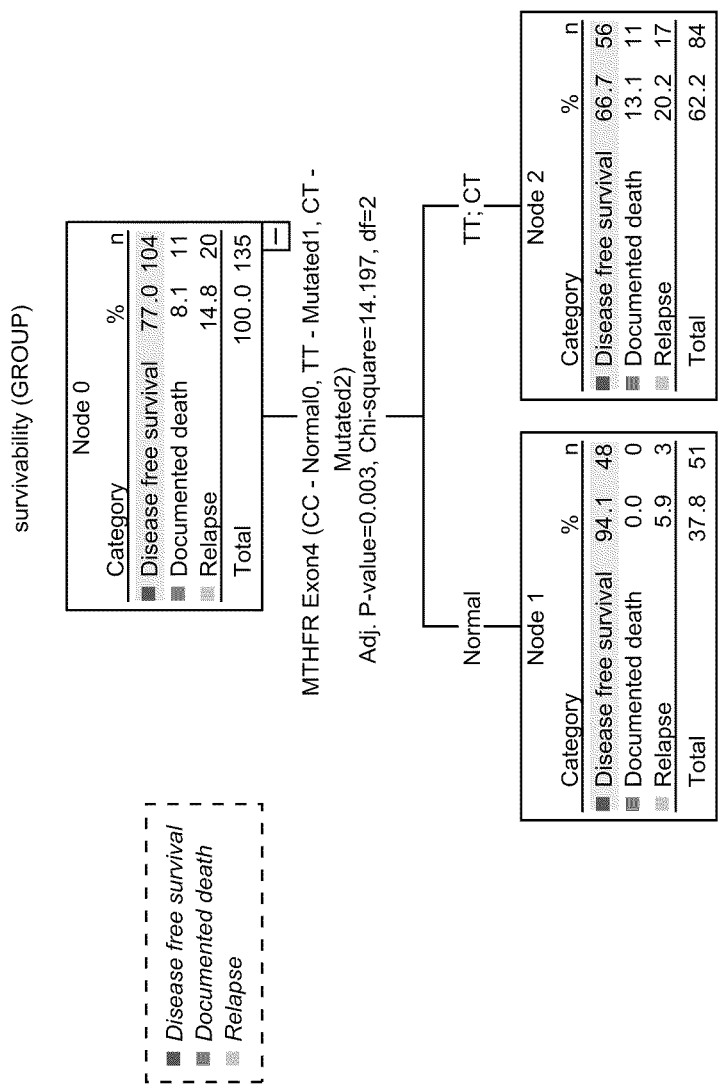
FIG. 14 shows an illustrative classification tree constructed using CHAID for survivability of acute lymphocytic leukemia ("ALL") according to methylenetetrahydrofolate ("MTHFR") Exon 4 genotype.

CHAID was used to construct a classification tree for survivability with different factors including genotype variation of different genes, age and class of leukemia, gender, chromosomal abnormalities, DNA damage and genotypes. CHAID showed that the MTHFR Exon 4 genotypes were highly associated with survivability of the ALL cases. FIG. 14 illustrates the classification tree constructed using CHAID showing survivability of ALL according to MTHFR Exon 4 genotype. The data was analyzed with Interactive CHAID in STATISTICA, and the tree graph showed that the algorithm has classified the data with significant p-values (0.003) and chi-square value (14.197) at 2 degrees of freedom.

Discriminant analysis was performed as function coefficients classification for survivability of ALL: (1) Resistance, (2) Relapse and (3) Disease free survival. Several variables were analyzed, including age, gender group, DNA tail length, FAB type, GST M1, GST T1 present or absent, SNPs in MTHFR exon 4, exon 7, DPD mutation, FLT3/ITD mutation, Karyotyping, and therapeutic drugs used.

The classification coefficients obtained are shown in Table 3.

TABLE 3

Classification Function Coefficients

| | survivability (GROUP) | | |
|---|---|---|---|
| Study Characters | Documented death | Relapse | Disease free survival |
| AGE | 1.240 | 1.521 | 1.227 |
| DNA Length CA (μm) | −29.075 | −18.572 | −19.885 |
| Gender Group | 7.656 | 5.985 | 6.422 |
| FAB Type Group | 59.224 | 37.731 | 36.544 |
| GST M1 (Present or Absent) | 7.412 | 7.888 | 7.963 |
| GST T1 (Present or Absent) | 6.365 | 6.307 | 6.445 |
| MTHFR Exon4 (CC - Normal 0, TT - Mutated 1, CT - Mutated 2) | 2.126 | 1.760 | 1.236 |
| MTHFR Exon7 (AA - Normal0, CC - Mutated1, AC - Mutated2) | 1.495 | 1.823 | 1.398 |
| DPD GROUP | 5.185 | 3.660 | 2.750 |
| FLT3 GROUP | −1.303 | −.375 | .560 |
| FLT3/ITD GROUP | −4.504 | −3.140 | −4.429 |
| Karyotyping (GROUP) | 3.877 | 1.537 | 1.266 |

TABLE 3-continued

| | Classification Function Coefficients | | |
| --- | --- | --- | --- |
| | survivability (GROUP) | | |
| Study Characters | Documented death | Relapse | Disease free survival |
| Drugs used (1, 2, 3, 4)* | 2.139 | 2.755 | 2.199 |
| (Constant) | −58.948 | −40.095 | −33.526 |

Fisher's linear discriminant functions
*Drug Groups:
1 = Vincristine, Methotrexate, Adriamycin, Daunomycin, Endoxon
2 = Vincristine, Methotrexate, Adriamycin, Endoxon, Doxorubicin
3 = Vincristine, Methotrexate, Adriamycin, Endoxon, Doxorubicin, Mercapto purine and 6 MP
4 = Vincristine, Adriamycin, Daunomycin, Endoxon, Doxorubicin The discriminate analysis showed that the classification was 80% correct for the originally classified values. An equation was developed for the prediction of the survivability by using longitudinal values:

$$Y(Score) = -58.948 + 2.139 \times (\text{Drugs used } 1,2,3,4)^* + 3.877 \times \text{Karyotyping}(1,0) - 4.504 \times \text{FLT/ITD}(1,0) - 1.303 \times \text{FLT3}(1,0) + 5.185 \times \text{DPD}(1,0) + 1.495 \times \text{MTHFR Exon7}(0,1,2) + 2.216 \times \text{MTHFR Exon4}(0,1,2) + 6.365 \times \text{GST T1}(1,0) + 7.412 \times \text{GST M1}(1,0) + 59.224 \times \text{FAB}(1,2,3) + 7.656 \times \text{Gender}(1,0) - 29.075 \times \text{DNA length(direct value)} + 1.24 \times \text{Age (Direct)}$$

A score in the range 0.064-3.458 indicates resistance to treatment when compared. A score in the range −0.484-0.063 is indicative of disease-free survival.

Table 4 below presents some of the prognostic factors and how they relate to prognosis.

TABLE 4

| Parameter | Finding | Prognosis |
| --- | --- | --- |
| age | <12 months | very poor |
| | 12-23 months | poor (?) |
| | 2-10 years | good |
| | >10 years | poor |
| initial white blood cell count | >200,000 per μL | very poor |
| | >50,000 per μL | poor |
| | <10,000 | good |
| sex | females | good |
| | males | poor |
| race | Blacks | poor |
| cytogenetics | hyperdiploidy (>50 chromosomes) | good |
| | hypoploidy | poor |
| | t (8; 14) | very poor (induction failure and early relapse) |
| | t (9; 22) (Philadelphia chromosome) | very poor (induction failure and early relapse) |
| | t (4; 11) | poor (induction failure and early relapse) |
| | dicentric translocation involving short arms of 9 and 12 | good |
| | t (1; 19) and pre-B immunophenotype (not early pre-B) | poor |
| | MLL gene rearrangement in infants | very poor |
| immunophenotype | early pre-B cell (no cytoplasmic immunoglobulin) | good |
| | pre-B cell (cytoplasmic immunoglobulin) | poor |
| | mature B cell | very poor |
| | T cell | poor |
| | myeloid markers present | poor |
| FAB morphology | L3 | poor |
| | L2 | poor |
| | L1 | good |
| mediastinal mass | present | poor |
| organomegaly | hepatomegaly | poor |
| | splenomegaly | poor |
| lymphadenopathy | present | poor |
| hemoglobin level | | |
| LDH | | |
| platelet count | | |
| serum immunoglobulins | low IgM | poor |
| | low IgG and/or IgA | poor |
| rapidity of leukemic cytoreduction on induction therapy | residual leukemia on day 14 of induction therapy | poor |
| response to initial course of induction chemotherapy | failure to achieve complete remission | poor |

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All references cited herein, including but not limited to patents, patent applications, and non-patent literature, are hereby incorporated by reference herein in their entirety.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A computer based method of predicting a prognosis of a patient having a multi-factored disease, disorder or condition, the method comprising:
receiving an input representative of one or more diagnostic factors of the multi-factored disease, disorder or condition;
constructing a classification tree of two or more diagnostic factors of the multi-factored disease, disorder or condition to detect an interaction between the two or more diagnostic factors;

performing a discriminant analysis, based at least in part on the classification tree, of the two or more diagnostic factors;

calculating a score using an equation based at least in part on the discriminant analysis; and predicting the prognosis of the patient based on the score, the input and the discriminant analysis of the two or more diagnostic factors.

2. The computer based method of claim 1, wherein receiving an input comprises:

receiving the input, the input representative of one or more diagnostic factors selected from physical attributes, genetic characteristics, demographic factors, environmental factors, physiological data, and symptoms.

3. The computer based method of claim 2, wherein at least one of the one or more diagnostic factors is a physical attribute selected from characteristics associated with disease state, body type, vision, strength, coordination, fertility, weight, skin, skeleto-muscular, longevity, and hair.

4. The computer based method of claim 2, wherein at least one of the one or more diagnostic factors is a genetic characteristic selected from gene sequences, mutations, abnormalities, inversions, insertions, deletions, substitutions, duplications, single nucleotide polymorphisms, haplotypes, centromeres, telomeres, methylation patterns, introns, and exons.

5. The computer based method of claim 2, wherein at least one of the one or more diagnostic factors is a demographic factor selected from race, ethnicity, age, sex, education level, income level, marital status, employment status, occupation, religion, location, family size, and exposure profile to environmental factors.

6. The computer based method of claim 2, wherein at least one of the one or more diagnostic factors is an environmental factor selected from stress, physical abuse, mental abuse, diet, maternal diet, infection, and exposure to carcinogens, toxins, pathogens, teratogens, radiation, or chemicals.

7. The computer based method of claim 2, wherein at least one of the one or more diagnostic factors is physiological data selected from heart rate, blood pressure, blood oxygen saturation, cardiac output, vascular activity, temperature, respiration, cardiac, abdominal, or breathing sounds, blood flow, hormonal concentration, enzyme and protein level, neural activity, electroencephalographic activity, and data associated with other electrical, mechanic, sonic, biochemical, or biophysical processes.

8. The computer based method of claim 2, wherein at least one of the one or more diagnostic factors is a symptom.

9. The computer based method of claim 1, wherein the multi-factored disease, disorder or condition is selected from cancers, autoimmune diseases, cardiovascular diseases, infectious diseases, endocrinological disorders, developmental abnormalities, mental disorders, neurological disorders, inflammatory disorders, and obesity and eating disorders.

10. The computer based method of claim 1, wherein the multi-factored disease, disorder or condition is selected from leukemia; cancers of the bladder, brain, breast, colon, esophagus, kidney, liver, lung, mouth, ovary, pancreas, prostate, skin, stomach and uterus; rheumatoid arthritis; multiple sclerosis; epilepsy; diabetes; osteoporosis; bipolar disorder; schizophrenia; atopy; inflammatory bowel disease; asthma; systemic lupus erythematosus; Grave's disease; angina pectoris; myocardial infarction; heart disease; cardiomyopathies; dsyrthythmias; AIDS; Lyme disease; bacterial meningitis; bacteremia and sepsis; sexually transmitted diseases; osteomyelitis; brain injuries, Parkinson's disease; Alzheimer's disease; congenital heart defects; neural tube defects; obesity and eating disorders.

11. The computer based method of claim 9, wherein the multi-factored disease, disorder or condition is a cancer.

12. The computer based method of claim 1, wherein calculating the score comprises a determination of a value of Y as:

$$Y(\text{Score}) = -58.948 + 2.139 \text{ drugs} + 3.877 * \text{Karyotyping} - 4.504 * \text{FLT/ITD} - 1.303 * \text{FLT3} + 5.185 * \text{DPD} + 1.495 * \text{MTHFR Exon 7} + 2.216 * \text{MTHFR Exon 4} + 6.365 * \text{GST T1} + 7.412 * \text{GST M1} + 59.224 * \text{FAB} + 7.656 * \text{gender} - 29.075 * \text{DNA length} + 1.24 * age;$$

wherein, drugs group=1, 2, 3, or 4;
Karyotyping group=1 or 0;
FLT/ITD group=1 or 0;
FLT3 group=1 or 0;
DPD group=1 or 0;
MTHFR Exon 7 is AA-Normal=0, CC-mutated=1, AC-mutated=2;
MTHFR Exon 4 is CC-Normal=0, TT-mutated=1, CT-mutated=2;
GST T1 is present=1, GST T1 not present=0;
GST M1 is present=1, GST M1 not present=0;
FAB group=1, 2, or 3;
male gender=1, female gender=0;
DNA length is in μm; and
age is in years.

13. The computer based method of claim 1, wherein predicting the prognosis of the patient further comprises comparing the score to a predetermined range of scores.

14. A computer program product for predicting a prognosis of a patient having a multi-factored disease, disorder or condition, the product comprising:

a nontransitory computer-readable storage medium bearing:

one or more instructions for receiving an input representative of one or more diagnostic factors of the multi-factored disease, disorder or condition;

one or more instructions for constructing a classification tree of two or more diagnostic factors of the multi-factored disease, disorder or condition to detect an interaction between the two or more diagnostic factors;

one or more instructions for performing a discriminant analysis, based at least in part on the classification tree, of the two or more diagnostic factors;

one or more instructions for calculating a score using an equation based at least in part on the discriminant analysis; and one or more instructions for predicting the prognosis of the patient based on, the score, the input and the discriminant analysis of the two or more diagnostic factors.

15. The computer program of claim 14, wherein the one or more instructions for constructing a classification tree of two or more diagnostic factors of the multi-factored disease, disorder or condition comprise:

one or more instructions for constructing the classification tree using Chi Square Automatic Interaction Detection (CHAID).

16. The computer program of claim 14, further comprising:

one or more instructions for generating a graphical illustration of at least one of (a) the classification tree of two or more diagnostic factors of the multi-factored disease, disorder or condition, and (b) the discriminant analysis of the two or more diagnostic factors.

17. The computer program of claim 16, wherein the one or more instructions for generating a graphical illustration of at least one of (a) the classification tree of two or more diagnostic factors of the multi-factored disease, disorder or condition, and (b) the discriminant analysis of the two or more diagnostic factors comprises:

one or more instructions for performing an analysis of at least one of the classification tree and the discriminant analysis; and one or more instructions for generating the graphical illustration based on the analysis.

18. The computer program of claim 14, further comprising: one or more instructions for generating a graphical illustration of the possible outcome.

19. The computer program of claim 18, wherein the one or more instructions for generating a graphical illustration of the possible outcome comprises:

one or more instructions for performing an analysis of the input and at least one of (a) the classification tree of two or more diagnostic factors of the multifactored disease, disorder or condition, and (b) the discriminant analysis of the two or more diagnostic factors; and one or more instructions for generating the graphical illustration based on the analysis.

20. A computer based system for predicting a prognosis of a patient having a multi-factored disease, disorder or condition, the system comprising:

a computing device configured to:
receive an input representative of one or more diagnostic factors of the multi-factored disease, disorder or condition;
construct a classification tree of two or more diagnostic factors of the multi-factored disease, disorder or condition to detect an interaction between two or more diagnostic factors;
perform a discriminant analysis, based at least in part on the classification tree, of the two or more diagnostic factors;
calculate a score using an equation based at least in part on the discriminant analysis; and
predict the prognosis of the patient based on, the score, the input and the discriminant analysis of the two or more diagnostic factors.

21. The computer based system of claim 20, wherein the computing device is further configured to construct the classification tree using Chi Square Automatic Interaction Detection (CHAID).

22. The computer based system of claim 20, wherein the computing device is further configured to determine a graphical illustration of at least one of (a) the classification tree of two or more diagnostic factors of the multi-factored disease, disorder or condition, and (b) the discriminant analysis of the two or more diagnostic factors.

* * * * *

UNITED STATES PATENT AND TRADEMARK OFFICE
CERTIFICATE OF CORRECTION

PATENT NO. : 8,639,639 B2
APPLICATION NO. : 12/624374
DATED : January 28, 2014
INVENTOR(S) : Jamil et al.

It is certified that error appears in the above-identified patent and that said Letters Patent is hereby corrected as shown below:

On Title Page 2, in item (56), under "OTHER PUBLICATIONS", in Column 1, Line 35, delete "Marrow.Cells" and insert -- Marrow Cells --, therefor.

In the Specification

In Column 1, Line 5, delete "APPLICATIONS" and insert -- APPLICATION --, therefor.

In Column 2, Line 24, delete "infarcation," and insert -- infarction, --, therefor.

In Column 2, Line 25, delete "dsyrthythmias)," and insert -- dysrhythmias), --, therefor.

In Column 3, Line 22, delete "an predicted" and insert -- a predicted --, therefor.

In Column 7, Line 18, delete "QUEST" and insert -- "QUEST" --, therefor.

In Column 8, Line 49, delete "infarcation;" and insert -- infarction; --, therefor.

In Column 8, Line 50, delete "dsyrthythmias;" and insert -- dysrhythmias; --, therefor.

In Column 9, Line 3, delete "change" and insert -- chance --, therefor.

In Column 10, Line 57, delete "and or" and insert -- and/or --, therefor.

In Column 13, Line 49, delete "infarcation;" and insert -- infarction; --, therefor.

In Column 13, Line 50, delete "dsyrthythmias;" and insert -- dysrhythmias; --, therefor.

Signed and Sealed this
First Day of July, 2014

Michelle K. Lee
*Deputy Director of the United States Patent and Trademark Office*

CERTIFICATE OF CORRECTION (continued)

In Column 16, Lines 59-60, delete "computer program 1000 products" and insert -- computer program products 1000 --, therefor.

In Column 17, Line 13, delete "computer program 1200 products" and insert -- computer program products 1200 --, therefor.

In Column 17, Line 14, delete "1006," and insert -- 1206, --, therefor.

In Column 19, Line 3, delete "device." and insert -- device). --, therefor.

In Column 19, Line 43, delete "device." and insert -- device). --, therefor.

In Column 21, Line 58, delete "abbarent" and insert -- aberrant --, therefor.

In Column 21, Line 64, delete "adapted" and insert -- adopted --, therefor.

In Column 21, Line 65, delete "al," and insert -- al., --, therefor.

In Column 21, Line 66, delete "al" and insert -- al., --, therefor.

In Column 21, Line 67, delete "al" and insert -- al., --, therefor.

In Column 24, Line 62, delete "and or" and insert -- and/or --, therefor.

In the Claims

In Column 26, Line 61, in Claim 1, delete "an-input" and insert -- an input --, therefor.

In Column 27, Line 65, in Claim 10, delete "infarcation;" and insert -- infarction; --, therefor.

In Column 27, Line 66, in Claim 10, delete "dsyrthythmias;" and insert -- dysrhythmias; --, therefor.

In Column 28, Line 37, in Claim 14, delete "nontransitory" and insert -- non-transitory --, therefor.

In Column 29, Line 21, in Claim 19, delete "multifactored" and insert -- multi-factored --, therefor.

UNITED STATES PATENT AND TRADEMARK OFFICE
CERTIFICATE OF CORRECTION

| | | |
|---|---|---|
| PATENT NO. | : 8,639,639 B2 | Page 1 of 1 |
| APPLICATION NO. | : 12/624374 | |
| DATED | : January 28, 2014 | |
| INVENTOR(S) | : Jamil et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1070 days.

Signed and Sealed this
Twenty-third Day of June, 2015

Michelle K. Lee
*Director of the United States Patent and Trademark Office*